(12) United States Patent
Panda

(10) Patent No.: US 11,584,725 B2
(45) Date of Patent: Feb. 21, 2023

(54) PYRAZINOIC ACID CONJUGATES AND HYBRID CONJUGATES

(71) Applicant: Augusta University Research Institute, Inc., Augusta, GA (US)

(72) Inventor: Siva Panda, Augusta, GA (US)

(73) Assignee: AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 0 days.

(21) Appl. No.: 16/674,651

(22) Filed: Nov. 5, 2019

(65) Prior Publication Data

US 2020/0140397 A1    May 7, 2020

Related U.S. Application Data

(60) Provisional application No. 62/756,430, filed on Nov. 6, 2018.

(51) Int. Cl.

| | |
|---|---|
| *C07D 241/24* | (2006.01) |
| *C07D 401/12* | (2006.01) |
| *C07D 413/12* | (2006.01) |
| *A61P 31/06* | (2006.01) |
| *C07D 401/14* | (2006.01) |
| *A61K 9/00* | (2006.01) |

(52) U.S. Cl.
CPC ............ *C07D 241/24* (2013.01); *A61P 31/06* (2018.01); *C07D 401/12* (2013.01); *C07D 401/14* (2013.01); *C07D 413/12* (2013.01); *A61K 9/0053* (2013.01)

(58) Field of Classification Search
CPC .. C07D 241/24; C07D 401/12; C07D 401/14; C07D 413/12; A61P 31/06
See application file for complete search history.

(56) References Cited

FOREIGN PATENT DOCUMENTS

CN          103030656         *  4/2013   ............... C07F 5/02

OTHER PUBLICATIONS

Panda et al., RSC Adv., 2019, 9, 20450-20462.*
STN Registry entry for CAS RN 114457-94-2, Entered STN May 14, 1988, Accessed May 22, 2021.*
STN Registry entry for CAS RN 1101675-82-4, Entered STN Feb. 6, 2009, Accessed May 7, 2022.*
STN Registry entry for CAS RN 323197-58-6, Entered STN Feb. 22, 2001, Accessed Aug. 12, 2022.*
Khalaf et al., Medicinal Chemistry Research 24, 2529-2550 (2015).*
Devarapalli, et al., "Design and Synthesis of Pyrazinoic acid-Isoniazid Hybrid Conjugates as Potential Anti-tubercular Agents", Abstract and poster presented at the Southeastern Regional meeting of the American Chemical Society (SERMACS), Charlotte, NC, Nov. 8, 2017.
Devarapalli, et al., "Design, Synthesis and 3D Pharmacophore Studies of Pyrazinoic Acid-Isoniazid Hybrid Conjugates as Potential Anti-Tubercular Agents", Abstract and poster presented at the Annual Florida Heterocyclic and Synthetic Conference, Gainesville, FL, Mar. 4, 2018.
Panda, et al., "Efficient Synthesis of Pyrazinoic Acid Hybrid Conjugates," Syn Open, 1:50-58 (2017).

* cited by examiner

*Primary Examiner* — Alicia L Otton
(74) *Attorney, Agent, or Firm* — Smith, Gambrell & Russell; Judy Jarecki-Black; Ram W. Sabnis

(57) ABSTRACT

Pyrazinamide (PZA) conjugates and hybrids are provided herein. The PZA conjugates are useful for treating bacterial infections. In one embodiment, the PZA conjugates are useful for treating tuberculosis.

17 Claims, 34 Drawing Sheets

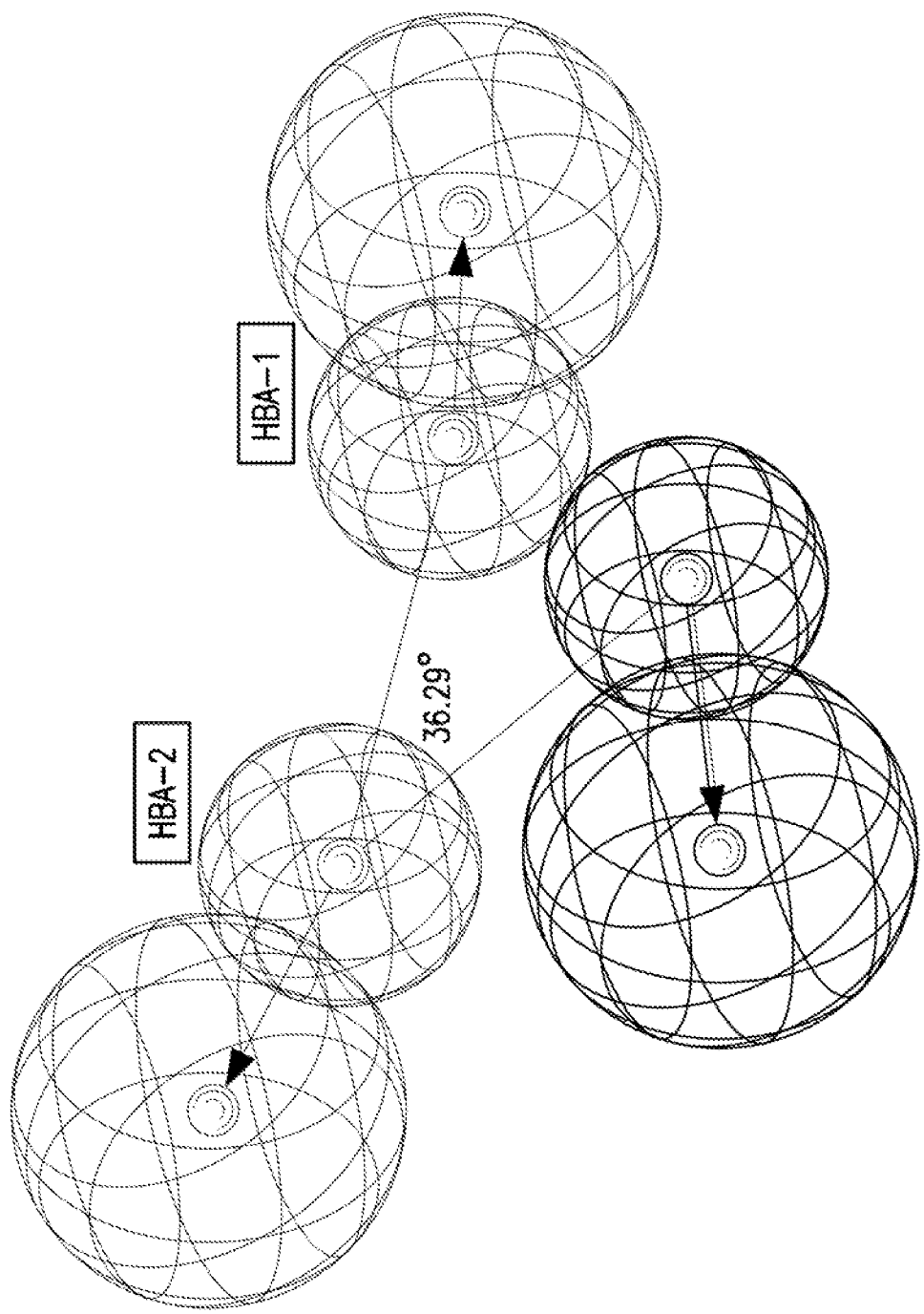

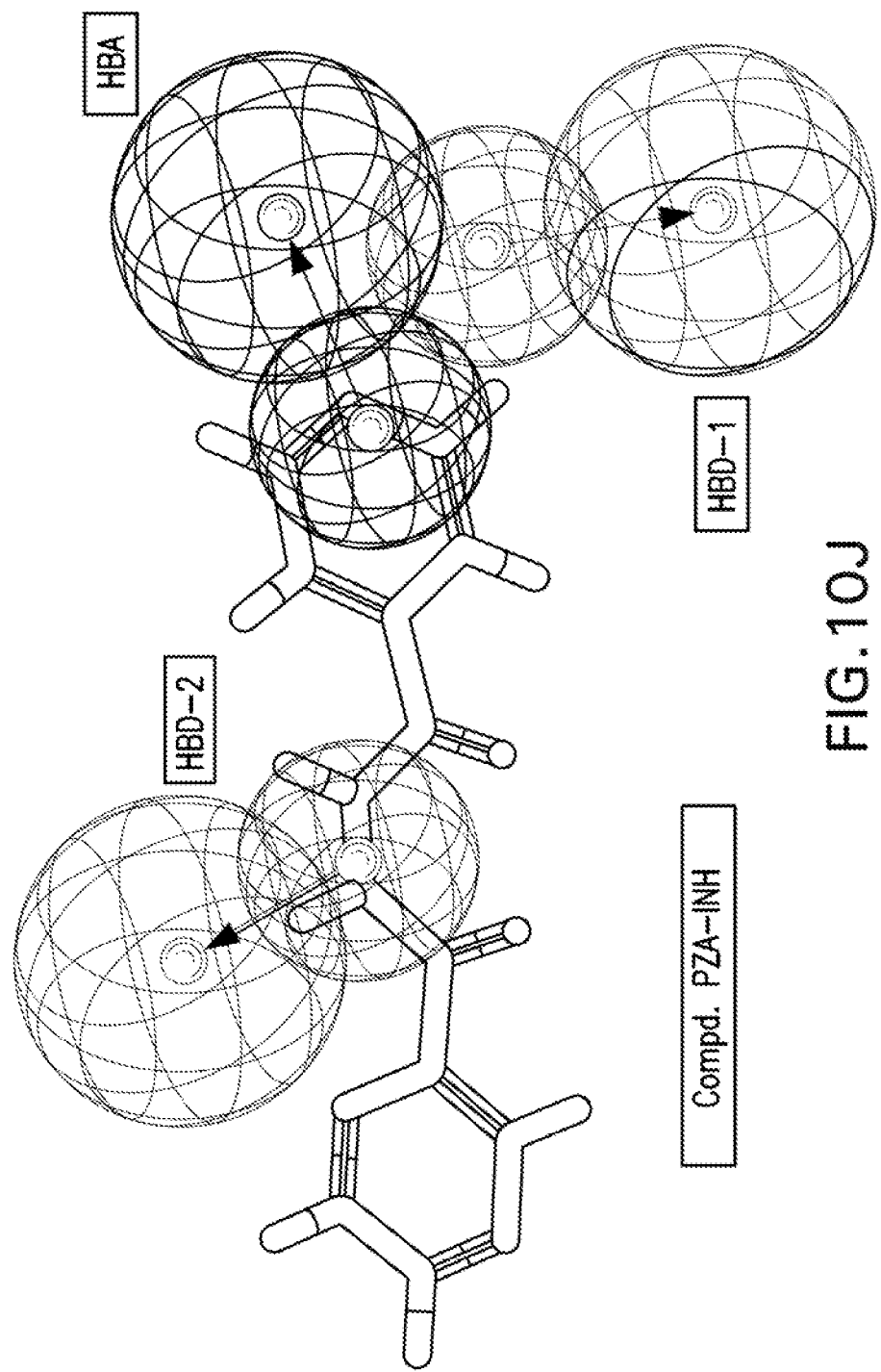

PYRAZINOIC ACID CONJUGATES AND HYBRID CONJUGATES

CROSS-REFERENCE TO RELATED APPLICATIONS

This application claims priority to and benefit of U.S. Provisional Patent Application No. 62/756,430 filed on Nov. 6, 2018, which is incorporated by reference in its entirety.

TECHNICAL FIELD OF THE INVENTION

Aspects of the invention are generally directed to antibiotic compositions and methods of their use.

BACKGROUND OF THE INVENTION

Tuberculosis (TB) is a bacterial pathogen caused by *Mycobacterium tuberculosis*, which is known to cause pulmonary infection and to become extremely pervasive within the lungs. TB is considered to be one of the world's deadliest communicable diseases because of its high virulence and the ability of *M. tuberculosis* to enter into a dormant state, then subsequently undergo reactivation. Pyrazinamide (PZA) is a first-line antituberculosis prodrug that is often used in combinational therapy with drugs such as isoniazide, ethambutol, streptomycin, and rifampicin.

PZA is perceived to inhibit vital ribosomal proteins after being converted into its active constituent, pyrazinoic acid (POA), by the tuberculosis enzyme, pyrazinamidase (PZAase) (FIG. 1A). It may lower the pH of the area surrounding *M. tuberculosis* to such an extent that the organism is unable to grow. Due to its low lipophilicity, POA cannot be absorbed by the gastrointestinal tract. Fortunately, the drug can be absorbed in the pyrazinamide configuration.

One of the drawbacks of using PZA to treat TB is that it inhibits protein synthesis. With prolonged administration of the recommended dose, harmful side effects such as hepatitis, acute hypertension, thrombocytopenia, and gastrointestinal discomfort have been reported. To overcome these issues, several molecular hybridization approaches have been reported for the development of potential antitubercular agents. Most hybridized structures include clinically used drugs such as rifamycin, ethambutol and isoniazid coupled with other hydrophobic structures such as cinnamic acid derivatives. Unfortunately the most promising prodrugs of POA are not stable.

Therefore, it is an object of the invention to provide improved prodrugs of POA methods of their use.

SUMMARY OF THE INVENTION

Pyrazinamide (PZA) conjugates and hybrids are provided herein. The PZA conjugates are useful for treating bacterial infections. In one embodiment the PZA conjugates are used to treat tuberculosis. An exemplary PZA conjugate has the generic structure

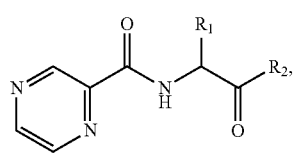
(1)

wherein:

$R_1$ is alkyl, alkenyl, alkynyl, aryl, or heteroaryl having between $C_1$ and $C_{30}$ carbon atoms, and $R_2$ is carboxylic acid, nicotinic acid, or derivatives thereof.

In one embodiment, $R_1$ is $CH_2CH(CH_3)_2$, $CH(CH_3)_2$, $CH(CH_2CH_3)CH_3$, $CH_2CH_2SCH_3$, $CH_2Ph$, or $CH_2$-indoyl. In one embodiment, $R_2$ is isoniazid or ethionamide.

Another embodiment provides a PZA conjugate having a structure according to any one of the following:

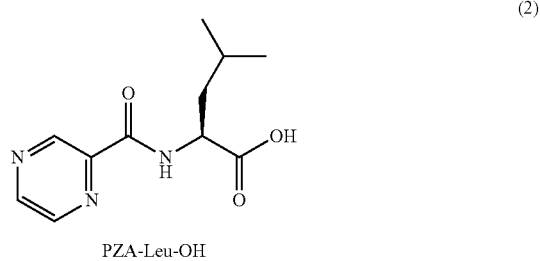
(2)
PZA-Leu-OH

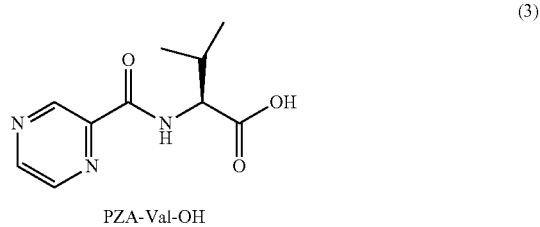
(3)
PZA-Val-OH

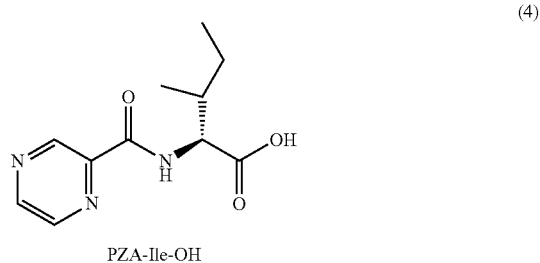
(4)
PZA-Ile-OH

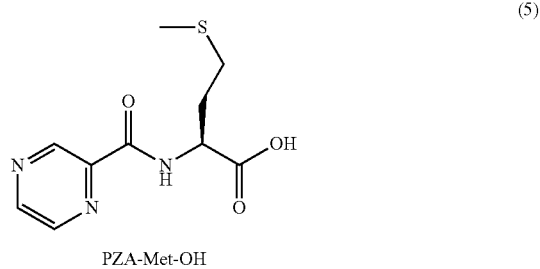
(5)
PZA-Met-OH

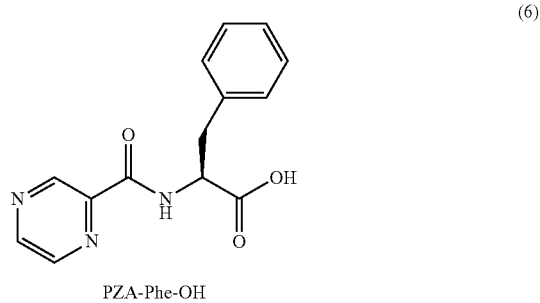
(6)
PZA-Phe-OH (7)
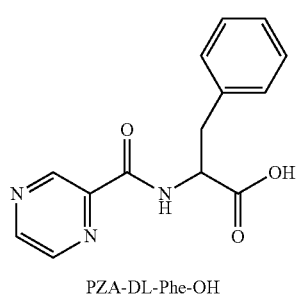
PZA-DL-Phe-OH
(8)
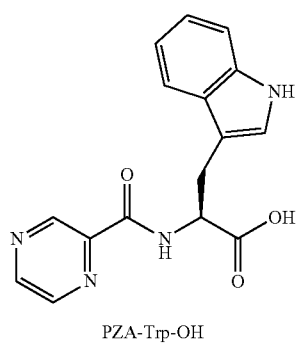
PZA-Trp-OH
(9)
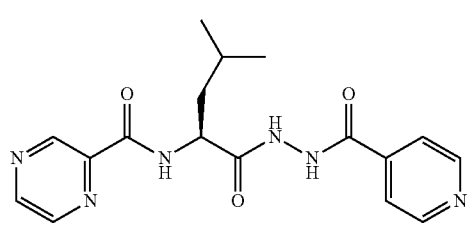
PZA-Leu-INH
(10)
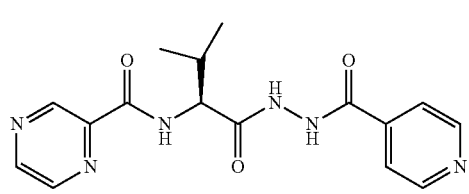
PZA-Val-INH
(11)
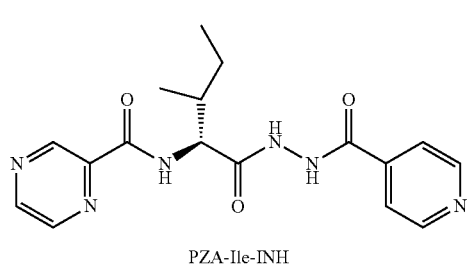
PZA-Ile-INH
(12)
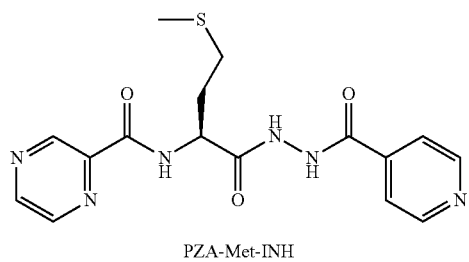 [SMILES: CSCC[C@H](NC(=O)c1cnccn1)C(=O)NNC(=O)c1ccncc1]
PZA-Met-INH
(13)
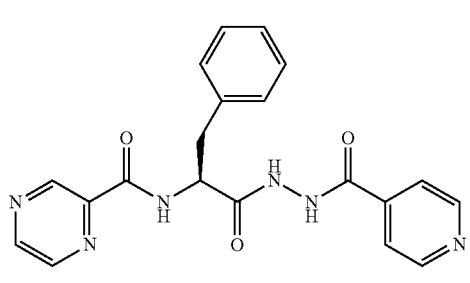
PZA-Phe-INH
(14)
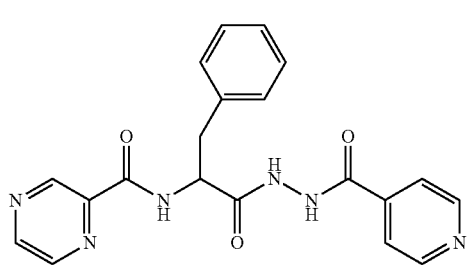
PZA-DL-Phe-INH
(15)
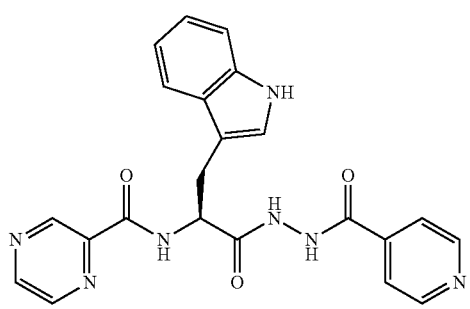
PZA-Trp-INH
(16)
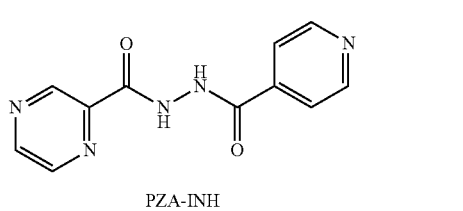 [SMILES: O=C(NNC(=O)c1cnccn1)c1ccncc1]
PZA-INH
(17)
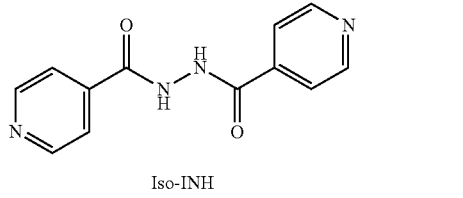 [SMILES: O=C(NNC(=O)c1ccncc1)c1ccncc1]
Iso-INH
(18)
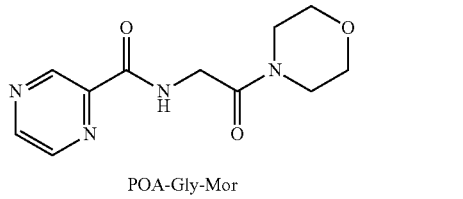
POA-Gly-Mor

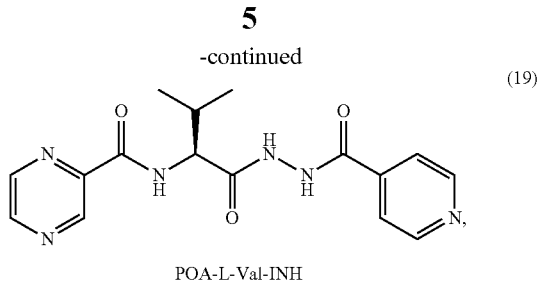

POA-L-Val-INH (19)

or an isolated optical isomer or an isolate isomer thereof.

Yet another embodiment provides pharmaceutical compositions including the disclosed PZA conjugates and hybrids. The pharmaceutical composition can be formulated for oral administration. In another embodiment, the pharmaceutical composition additionally includes a pharmaceutically acceptable excipient.

Also disclosed is a method for treating a bacterial infection in a subject in need thereof by administering to the subject an effective amount of a pharmaceutical composition including at least one of the disclosed PZA conjugates and hybrids. In one embodiment, the bacterial infection is tuberculosis. In another embodiment, the bacterial infection is cause by one or more bacteria selected from the group consisting of *Mycobacterium marinum*, *Mycobacterium fortuitum*, *Mycobacterium tuberculosis*, *Staphylococcus aureus*, *Enterococcus faecalis*, *Klebsiella pneumonia*, *Proteus vulgaris*, *Pseudomonas aeruginosa*, and *Proteus vulgaris*. In one embodiment, the composition is administered to the subject according to a regimen selected from 7 days per week for 8 weeks, 5 days per week for 8 weeks, 3 times per week for 7 weeks, or 7 days per week for 2 weeks then twice weekly for 6 weeks. In some embodiments, a second therapeutic is jointly administered to the subject serially or in combination or alternation with the pyrazinamide conjugate.

BRIEF DESCRIPTION OF THE DRAWINGS

FIGS. 7A and 7B are illustrations showing the constraint distances (FIG. 7A; HBA-1–HBA-2=4.800, HBA-1–HBD=3.026, HBA-2–HBD=4.909 Å) and constraint angles (FIG. 7B; HBA-1–HBA-2–HBD=36.29°) of the generated 3D-pharmacophore for the synthesized bio-active compounds against *Mycobacterium marinum* which contains two hydrogen bonding acceptors (HBA-1, HBA-2) and one hydrogen bonding donor (HBD).

FIGS. 8A-8K are illustrations showing the 3D-pharmacophore mapped on the synthesized bio-active compounds against *Mycobacterium marinum* (FIG. 8A=PZA; FIG. 8B=INH; FIG. 8C=PZA-Leu-OH; FIG. 8D=PZA-Leu-INH; FIG. 8E=PZA-Val-INH; FIG. 8F=PZA-Ile-INH; FIG. 8G=PZA-Met-INH; FIG. 8H=PZA-Phe-INH; FIG. 8I=PZA-Trp-INH; FIG. 8J=PZA-INH; FIG. 8K=Iso-INH).

FIGS. 10A-10K are illustrations showing the 3D-pharmacophore mapped on the synthesized bio-active compounds against *Mycobacterium fortuitum* (FIG. 10A=PZA; FIG. 10B=INH; FIG. 10C=PZA-Leu-OH; FIG. 10D=PZA-Leu-INH; FIG. 10E=PZA-Val-INH; FIG. 10F=PZA-Ile-INH; FIG. 10G=PZA-Met-INH; FIG. 10H=PZA-Phe-INH; FIG. 10I=PZA-Trp-INH; FIG. 10J=PZA-INH; FIG. 10K=Iso-INH).

DETAILED DESCRIPTION OF THE INVENTION

I. Definitions

Figure 1A:
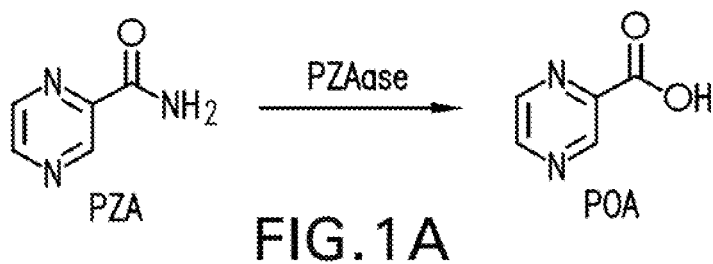
FIG. 1A is a schematic illustrating the hydrolysis of PZA into its active constituent pyrazinoic acid.
Figure 1B:
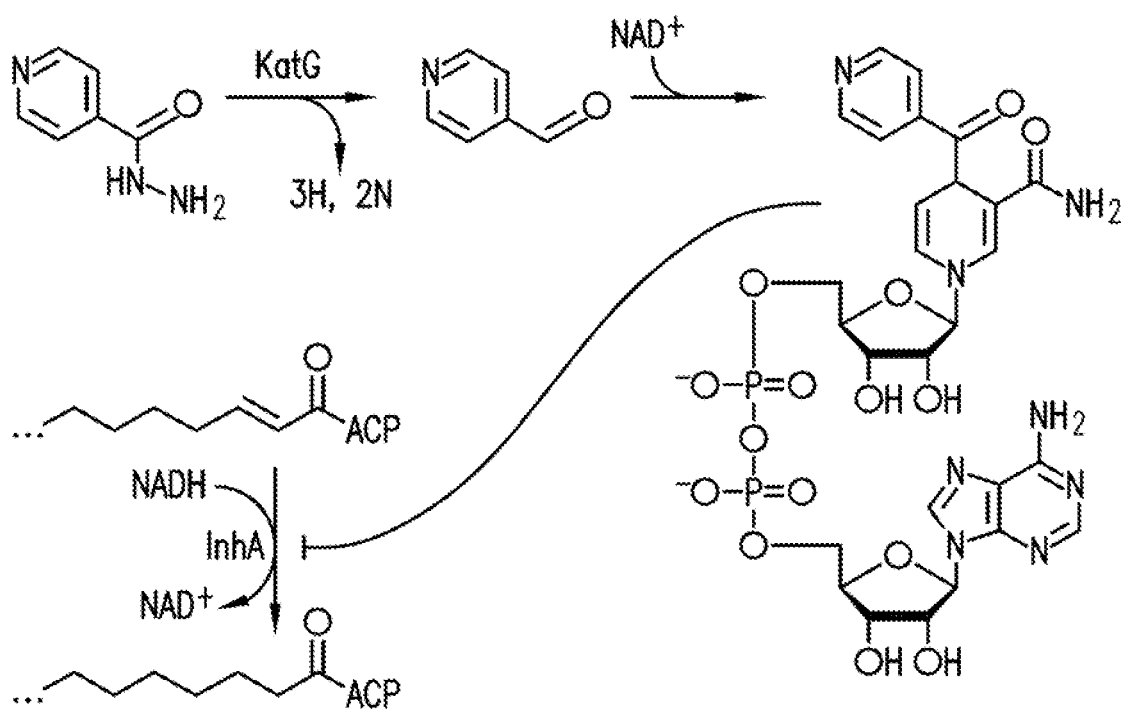
FIG. 1B is a schematic illustrating the series of reactions that lead to the activation of isoniazid.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term, "alkyl," as used herein, refers to the radical of saturated or unsaturated aliphatic groups, including straight-chain alkyl, alkenyl, or alkynyl groups, branched-chain alkyl, alkenyl, or alkynyl groups, cycloalkyl, cyclcoalkenyl, cycloalkynyl groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone, preferably 20 or fewer, and more preferably 10 or fewer.

The term, "alkyl," also includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —$NR_1R_2$, wherein $R_1$ and $R_2$ are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —$CONR_2$, wherein R is hydrogen, alkyl, or aryl; azide, aralkyl, alkoxyl, imino, phosphonate, phosphinate, silyl, ether, sulfonyl, sulfonamido, heterocyclic, aromatic or heteroaromatic moieties, —$CF_3$; —CN; —$NCOCOCH_2CH_2$; —NCOCOCHCH; —NCS; and combinations thereof.

The terms "alkenyl" and "alkynyl", as used herein, refer to unsaturated aliphatic groups analogous in length and possible substitution to the alkyls described above, but that contain at least one double or triple bond respectively.

The term "aryl" refers to a mono- or multi-cyclic aromatic radical having in the range of 6 up to 30 carbon atoms such as phenyl, naphthyl, tetrahydronapthyl, indanyl, and biphenyl.

The term, "heteroaryl," as used herein, refers to straight or branched chain, or cyclic carbon-containing radicals, or combinations thereof, having 3 to 30 carbon atoms where one or more of the carbon atoms are replaced by heteroatoms. Suitable heteroatoms include, but are not limited to, O, N, Si, P and S, where the nitrogen, phosphorous and sulfur atoms are optionally oxidized, and the nitrogen heteroatom is optionally quaternized. One of the rings may also be aromatic. Examples of heterocyclic and heteroaromatic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

As used herein, "tuberculosis disease", "TB disease", and "TB" can be used interchangeably and refer to an active infection with *Mycobacterium tuberculosis*. The disease is typically initiated by the deposition of *M. tuberculosis* contained in aerosol droplets onto lung alveolar surfaces. If the patient's immune system cannot stop the bacteria from growing, the bacteria are able to multiply in the body and cause active disease and symptoms thereof. Symptoms of tuberculosis include but are not limited to persistent cough, constant fatigue, weight loss, loss of appetite, fever, coughing up blood, night sweats, and shortness of breath.

As used herein, "latent tuberculosis infection", "latent TB infection" and "latent infection" can be used interchangeably and refer to a condition in which a patient has an inactive, asymptomatic *M. tuberculosis* infection. These patients typically show no symptoms and cannot spread the disease to others.

As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the terms "individual," "host," "subject," and "patient" are used interchangeably and refer to a mammal, including, but not limited to, humans, rodents, such as mice and rats, and other laboratory animals.

The terms "treat," "treating," or "treatment" refer to alleviating, reducing, or inhibiting one or more symptoms or physiological aspects of a disease, disorder, syndrome, or condition. "Treatment" as used herein covers any treatment of a disease in a subject, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

II. PZA Conjugates and Hybrids

A. Compounds

Pyrazinamide (PZA) conjugates and hybrids are provided. One embodiment provides a compound according to the following general structure:

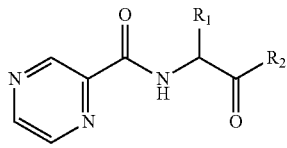
(1)

wherein $R_1$ is alkyl, alkenyl, alkynyl, aryl, or heteroaryl, having between $C_1$ and $C_{30}$ carbon atoms, and wherein $R_2$ is a hydroxyl group, or carboxylic acid, nicotinic acid or derivatives thereof.

In one embodiment, $R_1$ is $CH_2CH(CH_3)_2$, $CH(CH_3)_2$, $CH(CH_2CH_3)CH_3$, $CH_2CH_2SCH_3$, $CH_2Ph$, or $CH_2$-indoyl. In another embodiment, $R_2$ is isoniazid or ethionamide.

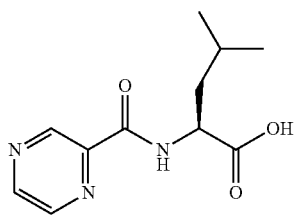
(2)

or an isolated optical isomer or an isolated enantiomer thereof. This compound is also referred to as PZA-Leu-OH.

Another embodiment provides a compound according to the following structure:

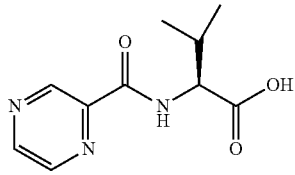
(3)

or an isolated optical isomer or an isolated enantiomer thereof. This compound is also referred to as PZA-Val-OH.

Another embodiment provides a compound according to the following structure:

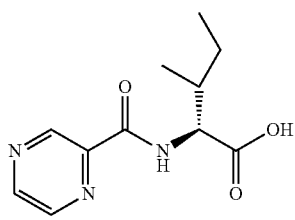
(4)

or an isolated optical isomer or an isolated enantiomer thereof. This compound is also referred to as PZA-Ile-OH.

Still another embodiment provides a compound according to the following structure:

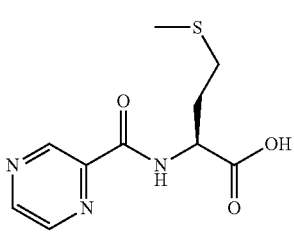
(5)

or an isolated optical isomer or an isolated enantiomer thereof. This compound is also referred to as PZA-Met-OH.

Yet another embodiment provides a compound according to the following structure:

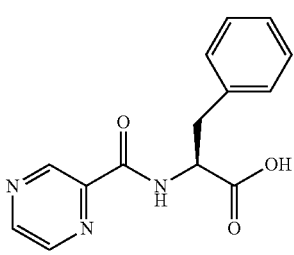
(6)

or an isolated optical isomer or an isolated enantiomer thereof. This compound is also referred to as PZA-Phe-OH.

One embodiment provides a compound according to the following structure:

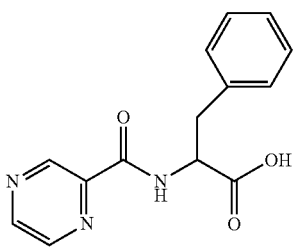
(7)

or an isolated optical isomer or an isolated enantiomer thereof. This compound is also referred to as PZA-DL-Phe-OH.

One embodiment provides a compound according to the following structure:

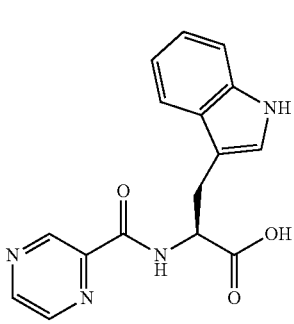
(8)

or an isolated optical isomer or an isolated enantiomer thereof. This compound is also referred to as PZA-Trp-OH.

Other embodiments provide PZA and isoniazide (INH) hybrid compounds. One embodiment provides a compound according to the following structure:

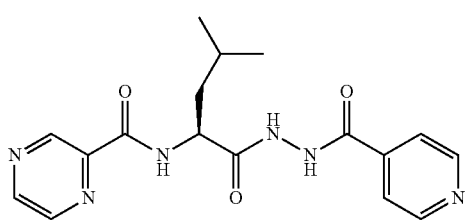
(9)

or an isolated optical isomer or an isolated enantiomer thereof. This compound is also referred to as PZA-Leu-INH.

One embodiment provides a compound according to the following structure:

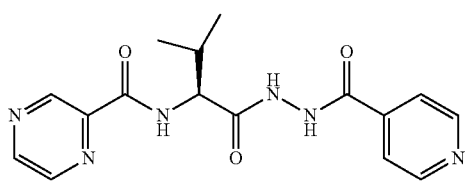
(10)

or an isolated optical isomer or an isolated enantiomer thereof. This compound is also referred to as PZA-Val-INH.

One embodiment provides a compound according to the following structure:

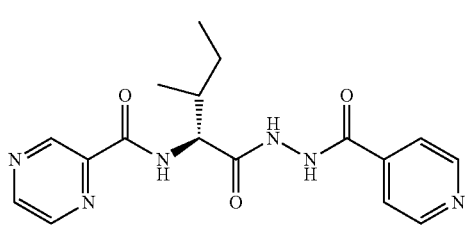
(11)

or an isolated optical isomer or an isolated enantiomer thereof. This compound is also referred to as PZA-Ile-INH.

One embodiment provides a compound according to the following structure:

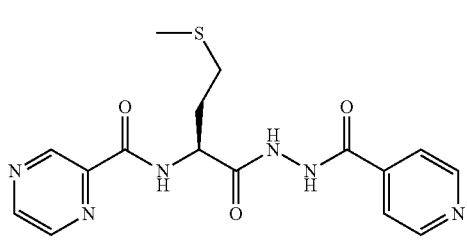
(12)

or an isolated optical isomer or an isolated enantiomer thereof. This compound is also referred to as PZA-Met-INH.

One embodiment provides a compound according to the following structure:

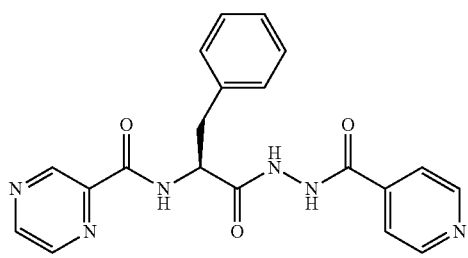
(13)

or an isolated optical isomer or an isolated enantiomer thereof. This compound is also referred to as PZA-Phe-INH.

One embodiment provides a compound according to the following structure:

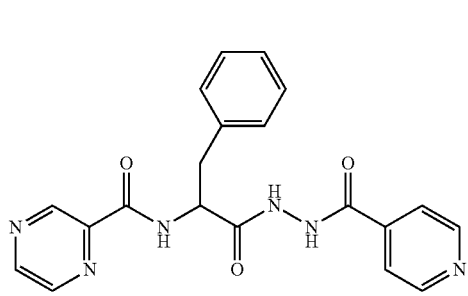
(14)

or an isolated optical isomer or an isolated enantiomer thereof. This compound is also referred to as PZA-DL-Phe-INH.

One embodiment provides a compound according to the following structure:

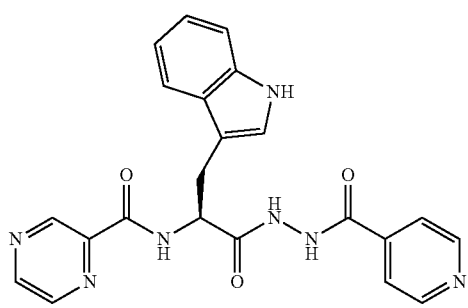
(15)

or an isolated optical isomer or an isolated enantiomer thereof. This compound is also referred to as PZA-Trp-INH.

One embodiment provides a compound according to the following structure:

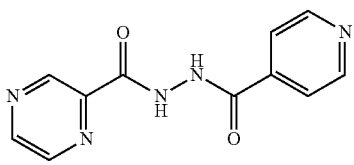

(16)

or an isolated optical isomer or an isolated enantiomer thereof. This compound is also referred to as PZA-INH.

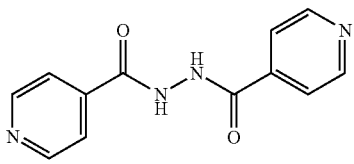

(17)

One embodiment provides a compound according to the following structure:

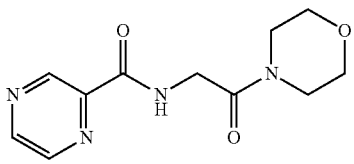

(18)

or an isolated optical isomer or an isolated enantiomer thereof. This compound is also referred to as Iso-INH.

One embodiment provides a compound according to the following structure:

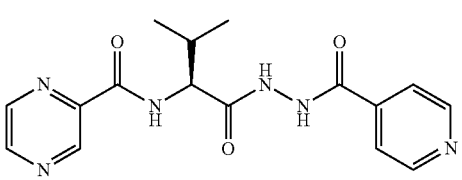

(19)

or an isolated optical isomer or an isolated enantiomer thereof. This compound is also referred to as POA-L-Val-INH.

In some embodiments, other isonicotinic acid derivatives are contemplated instead of INH. Exemplary isonicotinic acid derivatives include but are not limited to iproniazid, nialamide, ethionamide, and dexamethasone isonicotinate. In other embodiments, a nicotinic acid derivative is conjugated to PZA. Exemplary nicotinic acid derivatives include but are not limited to ethionamide.

B. Formulations and Pharmaceutical Compositions

In some embodiments the disclosed PZA conjugates and hybrids are formulated as a pharmaceutical formulation, optionally with a second antibiotic, antifungal agent, or other treatment for tuberculosis. Other antibiotics that are commonly used to treat bacterial infections include but are not limited to amoxicillin, ampicillin, flucoxacillin, penicillin, pivmecillinam, tazocin, timentin, cefaclor, cefadroxil, cephalexin, cefotaxime, cefradine, ceftazimide, ceftriaxone, cefuroxime, azithromycin, clamelle, clarithromycin, erythromycin, ciprofloxacin, levofloxacin, moxifloxacin, nalidixic acid, norfloxacin, ofloxacin, demeclocycline, doxycycline, lymecycline, minocycline, oxytetracycline, tetracycline, amikacin, gentamicin, neomycin, tobramycin, septrin, sulfadiazine, aztreonam, chloramphenicol, clindamycin, clofazimine, colistin, daptomycin, fidaxomicin, fucidin, linezolid, meropenem, methenamine, metronidazole, nitrofurantoin, primazin, rifaximin, teicoplanin, tinidazole, trimethoprim, and vancomycin.

Pharmaceutical compositions including the disclosed compositions are provided. Pharmaceutical compositions containing the disclosed compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed compositions, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed compositions, generally dosage levels of 0.001 to 20 mg/kg of body weight daily are administered to mammals. Generally, for intravenous injection or infusion, dosage may be lower.

In certain embodiments, the composition is administered locally, for example by injection directly into a site to be treated. Typically, the injection causes an increased localized concentration of the composition which is greater than that which can be achieved by systemic administration. The compositions can be combined with a matrix as described above to assist in creating an increased localized concentration of the polypeptide compositions by reducing the passive diffusion of the polypeptides out of the site to be treated.

In some embodiments, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more of the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

In embodiments the compositions are formulated for oral delivery. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The agents can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. Biochem. 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The agent can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects.

For oral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

The disclosed compositions can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations may require the inclusion of penetration enhancers.

The compositions disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl. Polymer Sci., 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods for Treating Infections

The disclosed compounds and compositions can be used to treat bacterial infections. One embodiment provides a method for treating a bacterial infection in a subject in need thereof by administering to the subject an effective amount of pharmaceutical composition containing an effective amount of one or more of the PZA conjugates and hybrids to treat the bacterial infection.

In some embodiments, the bacterial infection is caused by one or more bacteria selected from the group consisting of *Mycobacterium marinum, Mycobacterium fortuitum, Mycobacterium tuberculosis, Staphylococcus aureus, Enterococcus faecalis, Klebsiella pneumonia, Proteus vulgaris, Pseudomonas aeruginosa*, and *Proteus vulgaris*.

In one embodiment, the subject has or is suspected of having tuberculosis.

TB bacterial infection can be detected using the tuberculin skin test (TST) or interferon-gamma release assays (IGRAs) in combination with chest x-ray. The TST is used to determine if a person is infected with tuberculosis. If a person is infected, a delayed-type hypersensitivity reaction is detectable 2 to 8 weeks after infection. IGRAs are used to determine if a person is infected with tuberculosis by measuring the immune response to TB proteins in whole blood. Not everyone infected with TB bacteria becomes sick. Because of this, two TB-related conditions exist: latent TB infection and TB disease. Chest x-rays help differentiate between latent TB infection and TB disease in individuals who test positive for TB infection with TST or IGRA. Patients with latent disease do not have symptoms and they cannot spread TB bacteria to others. However, patients with latent disease must be treated to prevent the bacteria from becoming active and developing into TB disease. Groups that have a higher risk of developing TB disease from latent TB infection include but are not limited to patients with HIV, diabetes, and other conditions that affect the immune system. These high risk patients should be treated for latent infection. There are four CDC-recommended treatment regimens for latent TB infection. Treatment regimens for latent TB infection include but are not limited to isoniazid and rifapentine once weekly for 3 months, rifampin daily for four months, and isoniazid daily or twice weekly for six to 9 months.

When TB bacteria become active and the immune system cannot rid the body of the bacteria, the patient will develop TB disease. Tuberculosis drugs target various aspects of *Mycobacterium tuberculosis* biology, including inhibition of cell wall synthesis, protein synthesis, or nucleic acid synthesis. There are several drugs currently approved by the U.S. FDA for treating TB including but not limited to first-line anti-TB agents such as isoniazid, rifampin, ethambutol, and pyrazinamide. Second-line drugs for the treatment of tuberculosis that can be used with the PZA conjugates and hybrids include but are not limited to amikacin, kanamycin, streptomycin, cyclic peptides such as capreomycin, ethionamide, prothionamide, para-aminosalicylic acid (PAS), cycloserine, moxifloxacin, levofloxacin, and nitroimidazole. TB infection is typically treated by taking several drugs for six to nine months. Treatment regimens for treating TB disease have an intensive phase of two months, followed by a continuation phase of either four or seven months. During the intensive phase, patients commonly receive isoniazid, rifampin, ethambutol, and pyrazinamide for 7 days per week for 56 doses, 5 days per week for 40 doses, 3 times per week for 24 doses or 7 days per week for 14 doses then twice weekly for 12 doses. During the continuation phase, patients typically receive isoniazid and rifampin for 7 days per week for 126 doses, 5 days per week for 90 doses, 3 times per week for 54 doses, or twice weekly for 36 doses. In one embodiment, patients are administered an effective amount of pharmaceutical composition containing an effective amount of one or more of the PZA conjugates and hybrids for 7 days per week for 56 doses, 5 days per week for 40 doses, 3 times per week for 24 doses or 7 days per week for 14 doses then twice weekly for 12 doses. In another embodiment, the disclosed pharmaceutical compositions containing an effective amount of one or more of the PZA conjugates and hybrids treat TB disease without the need for a continuation phase of treatment.

In some embodiments, the subject has Multi-drug resistant (MDR) TB. MDR TB occurs when a *Mycobacterium tuberculosis* strain is resistant to at least isoniazid and rifampin. In order to treat and cure MDR TB disease, patients must be given a combination of second-line drugs. Second-line drugs may have more side-effects and the treatment must last longer than combination treatment with first-line drugs. Exemplary treatment for MDR TB includes but is not limited to 18-24 months of treatment with five or six drugs such as a susceptible first-line drugs plus an injectable agent, a fluoroquinolone, and other second-line drugs as needed. Extensively drug-resistant tuberculosis (XDR TB) is defined as MDR TB with additional resistance to any fluoroquinolone and to at least one of three injectable anti-TB drugs (i.e., kanamycin, amikacin, or capreomycin). In one embodiment, the disclosed pharmaceutical compositions containing an effective amount of one or more of the PZA conjugates and hybrids can treat MDR TB.

EXAMPLES

Example 1: Synthesis of PZA Conjugates

Figure 2:
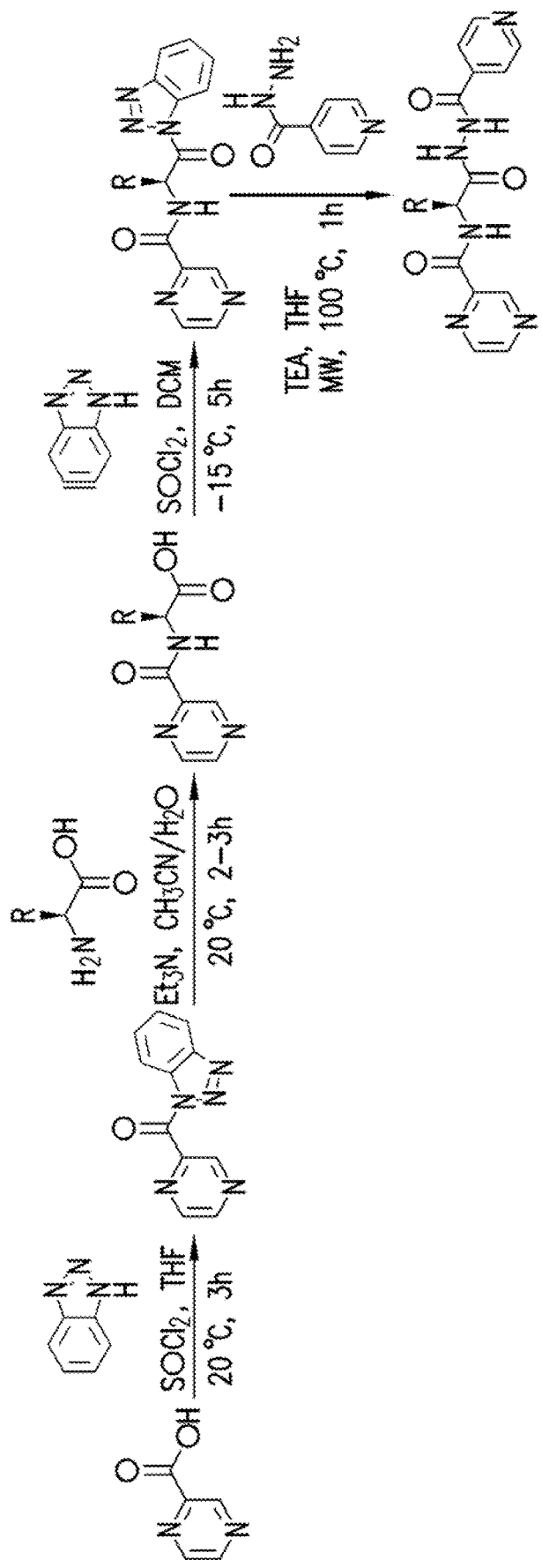
FIG. 2 is a schematic illustrating the synthesis of hybrid conjugates of pyrazinoic acid by coupling amino acid and isoniazid using benzotriazole chemistry.
Figure 3:
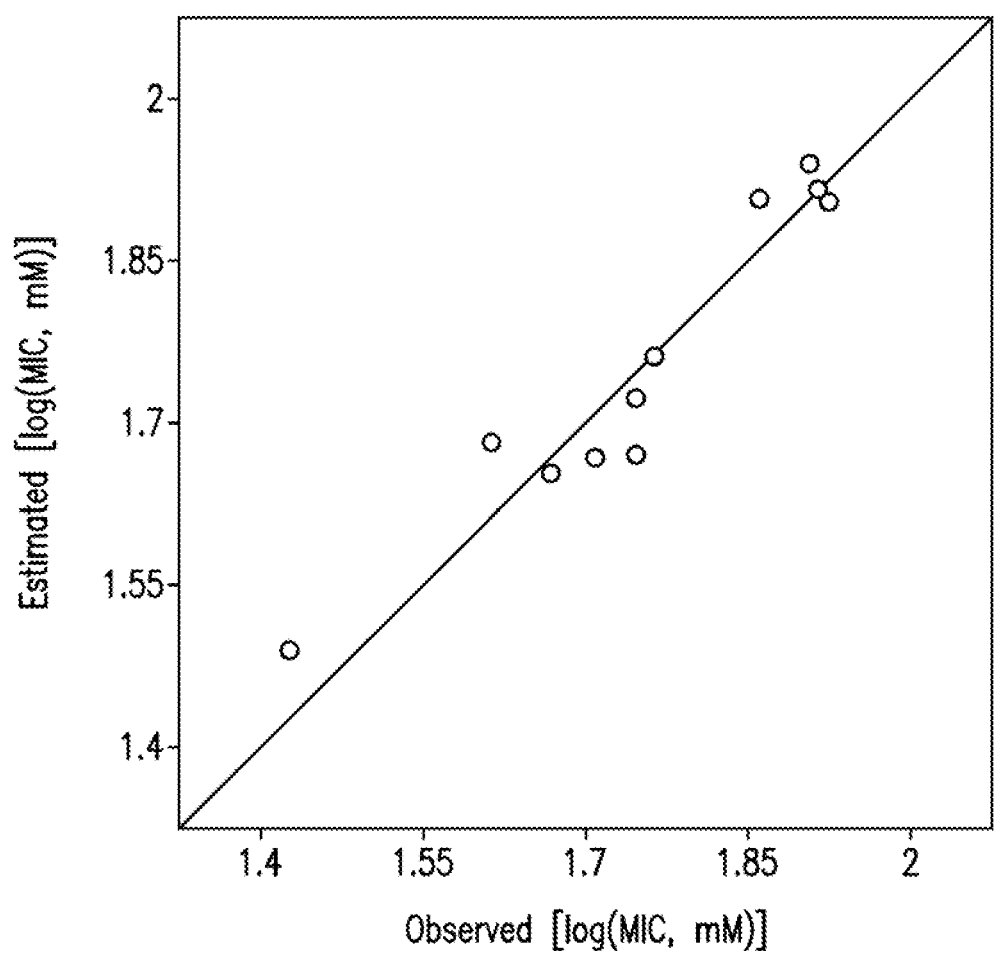
FIG. 3 is a BMLR-QSAR model plot of correlations representing the observed vs. predicted log(MIC, mM) values for the tested compounds against *Mycobacterium marinum*.
Figure 4:
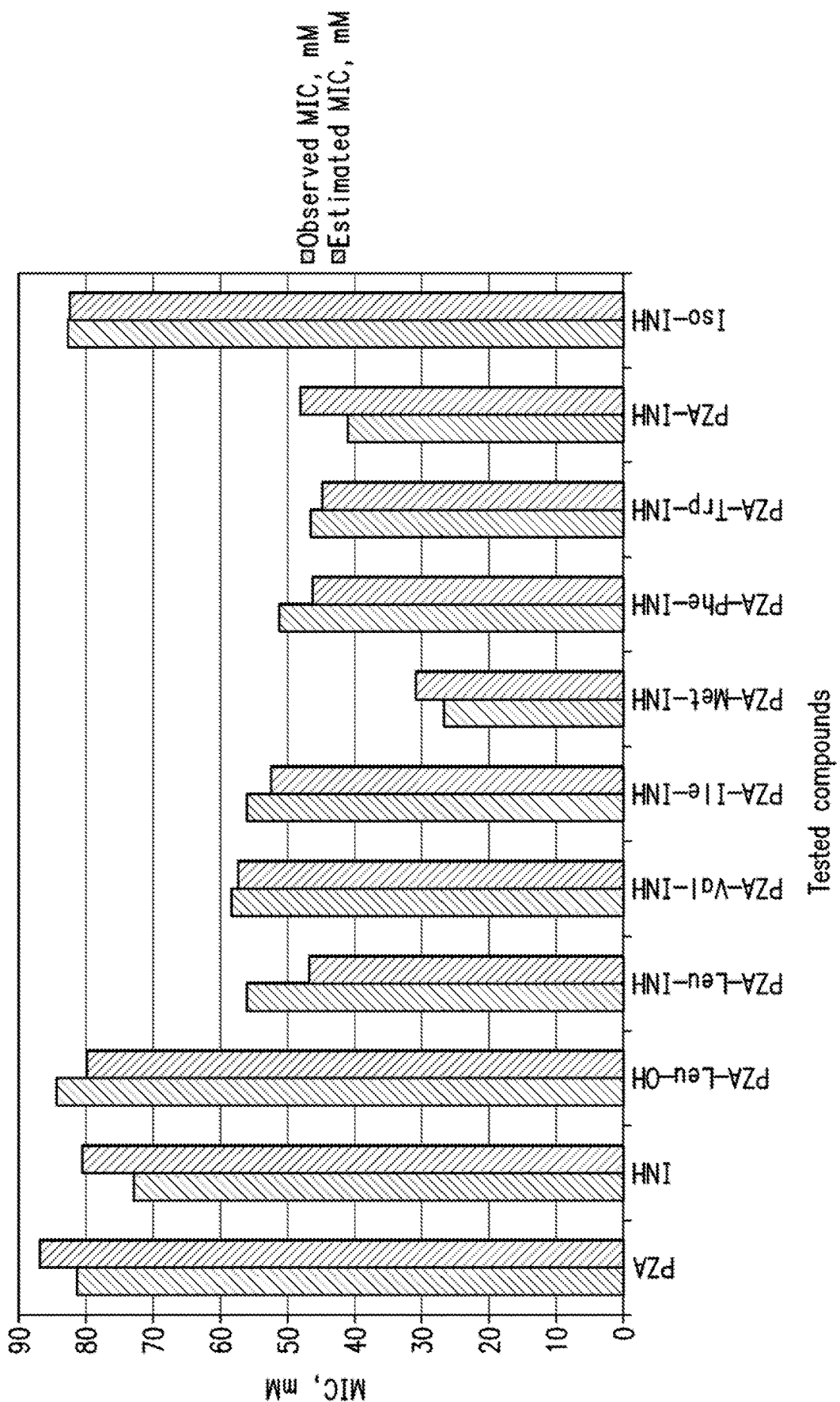
FIG. 4 is a bar graph showing observed and estimated activity MIC values for the tested compounds against *Mycobacterium marinum* according to the BMLR-QSAR model.
Figure 5:
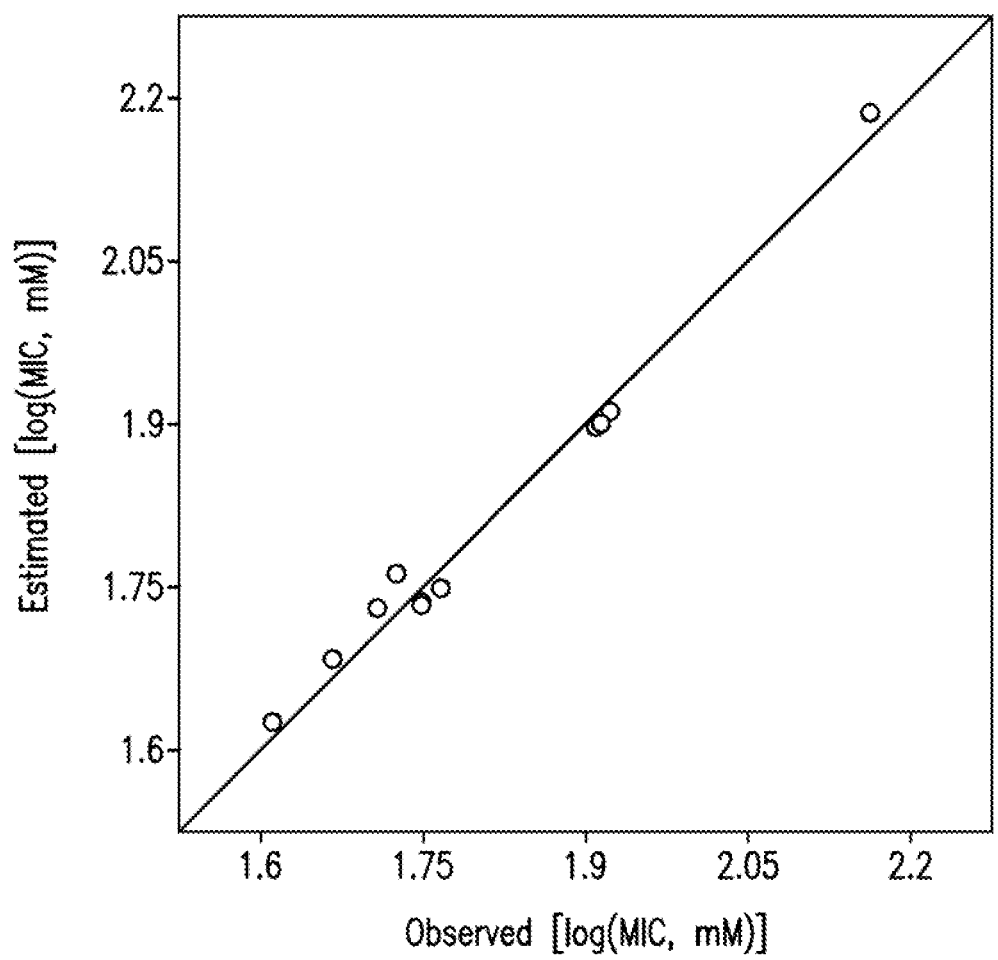
FIG. 5 is a BMLR-QSAR model plot of correlations representing the observed vs. predicted log(MIC, mM) values for the tested compounds against *Mycobacterium fortuitum*.
Figure 6:
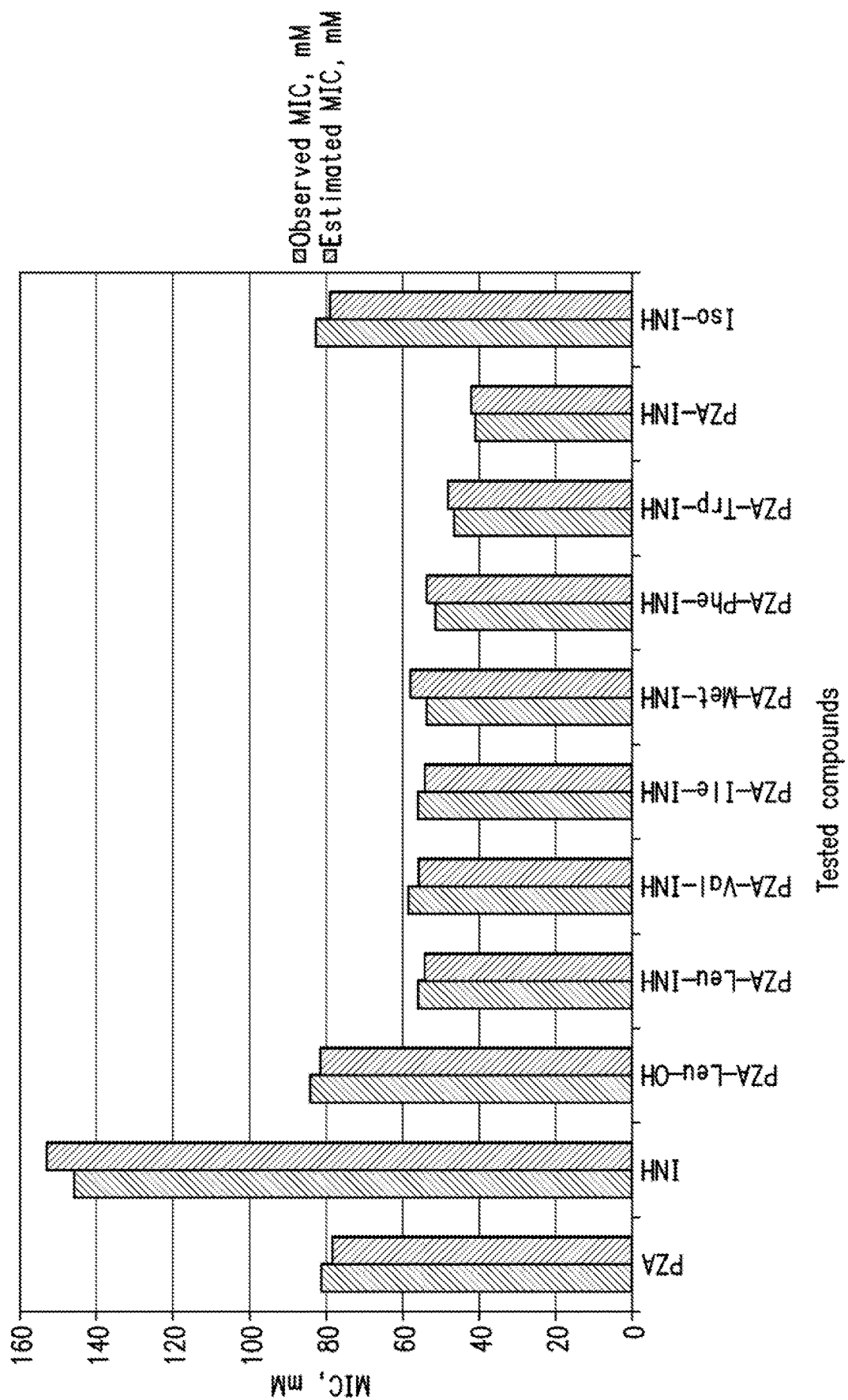
FIG. 6 is a bar graph showing the observed and estimated activity MIC values for the tested compounds against *Mycobacterium fortuitum* according to the BMLR-QSAR model.

Materials and Methods:

Hybrid conjugates of pyrazinoic acid were successfully synthesized by coupling an amino acid and then followed by the isoniazid using benzotriazole chemistry (FIG. 2). All the synthesized compounds were fully characterized by NMR and Mass spectroscopy. The retention of the chirality was studied by optical rotation and chiral HPLC of L and DL amino acid derivatives.

Results:

Benzotriazole chemistry was utilized to synthesize the desired hybrid conjugates. PZA-AA-INH conjugates were successfully synthesized in good yields (Table 1). The purity of the products was confirmed by spectral studies. Preservation of chirality from starting material to final products was validated by chiral HPLC and optical rotation.

TABLE 1

Properties of PZA-INH hybrid conjugates.

| Entry | Compounds | Yield (%) | mp (° C.) |
|---|---|---|---|
| 1 | PZA-L-Leu-OH | 77 | 115-117 |
| 2 | PZA-L-Ile-OH | 74 | 152-154 |
| 3 | PZA-L-Val-OH | 72 | 160-162 |
| 4 | PZA-L-Met-OH | 68 | 136-138 |
| 5 | PZA-L-Phe-OH | 89 | 165-167 |
| 6 | PZA-DL-Phe-OH | 90 | 155-157 |
| 7 | PZA-L-Trp-OH | 89 | 133-135 |
| 8 | PZA-L-Leu-INH | 69 | 161-163 |
| 9 | PZA-L-Ile-INH | 82 | 163-165 |
| 10 | PZA-L-Met-INH | 79 | 175-177 |
| 11 | PZA-L-Met-INH | 78 | oil |
| 12 | PZA-L-Phe-INH | 88 | 177-179 |

TABLE 1-continued

Properties of PZA-INH hybrid conjugates.

| Entry | Compounds | Yield (%) | mp (° C.) |
|---|---|---|---|
| 13 | PZA-DL-Phe-INK | 80 | 142-144 |
| 14 | PZA-L-Trp-INH | 81 | 159-161 |

Example 2: Aerobic Antibacterial Properties

Materials and Methods:

Antibacterial properties were investigated for the synthesized compounds against a variety of Gram-positive (*Staphylococcus aureus, Enterococcus faecalis*) and Gram-negative (*Klebsiella pneumonia, Proteus vulgaris, Pseudomonas aeruginosa*) bacteria utilizing the standard technique.

Results:

From the results obtained (Table 2) it has been noticed that most of the tested compounds (INH, PZA-INH, and Iso-INH are an exception) show potency in sub-micromolar values (MIC=0.97-0.07 μM), higher than that of the standard reference used (MIC of ciprofloxacin=1.21 μM) against *Enterococcus faecalis*. Similar observations were also shown for most of the tested compounds against *Proteus vulgaris* (PZA, INH, PZA-Leu-OH, PZA-DL-Phe-INH, and PZA-INH are exceptions) and *Pseudomonas aeruginosa* (PZA, INH, PZA-Val-OH, PZA-DL-Phe-OH, PZA-Leu-INH and PZA-DL-Phe-INH) with MIC values=0.12-0.27, 0.12-0.51 μM, respectively relative to the standard reference ciprofloxacin (MIC=6.04, 12.07 μM against *Proteus vulgaris* and *Pseudomonas aeruginosa*, respectively).

TABLE 2

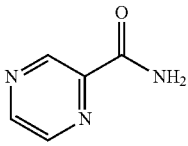

Antimicrobial properties of the tested compounds against aerobic bacteria.

| Entry | Compound | Minimum inhibitory concentration (MIC), μg/ml (μM) | | | | |
|---|---|---|---|---|---|---|
| | | *Staphylococcus aureas* | *Enterococcus faecalis* | *Klebsiella pneumonia* | *Proteus vulgaris* | *Pseudomonas aeruginosa* |
| 1 | Molecular weight: 123.1150 Pyrazine-2-carboxamide (pyrazinamide) | 1024 (8317.43) | 0.12 (0.97) | 64 (519.84) | 8 (64.98) | 4 (32.49) |
| 2 | Molecular weight: 137.1420 Isoniazid | 64 (466.67) | 16 (116.67) | 8 (58.33) | 64 (466.67) | 64 (466.67) |

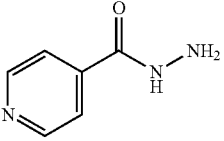

TABLE 2-continued

Antimicrobial properties of the tested compounds against aerobic bacteria.

| Entry | Compound | Minimum inhibitory concentration (MIC), µg/ml (µM) | | | | |
| --- | --- | --- | --- | --- | --- | --- |
| | | Staphylococcus aureas | Enterococcus faecalis | Klebsiella pneumonia | Proteus vulgaris | Pseudomonas aeruginosa |
| 3 | 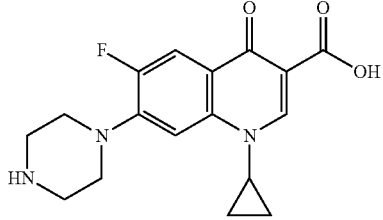<br>Molecular weight: 331.3474<br>Ciprofloxacin | 0.4 (1.21) | 0.4 (1.21) | 2 (6.04) | 2 (6.04) | 4 (12.07) |
| 4 | 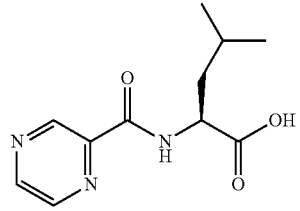<br>Molecular weight: 237.2590<br>PZA-Leu-OH | 1024 (4315.96) | 0.03 (0.13) | 64 (269.75) | 8 (33.72) | 0.03 (0.13) |
| 5 | 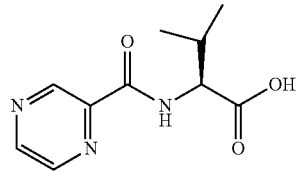<br>Molecular weight: 223.2320<br>PZA-Val-OH | 512 (2293.58) | 0.03 (0.13) | 0.03 (0.13) | 0.06 (0.27) | 4 (17.92) |
| 6 | 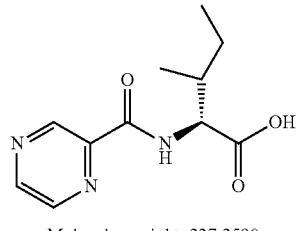<br>Molecular weight: 237.2590<br>PZA-Ile-OH | 16 (67.44) | 0.03 (0.13) | 8 (33.72) | 0.06 (0.25) | 0.12 (0.51) |
| 7 | 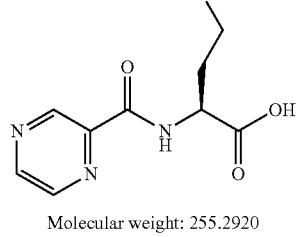<br>Molecular weight: 255.2920<br>PZA-Met-OH | 16 (62.67) | 0.03 (0.12) | 64 (250.69) | 0.06 (0.24) | 0.12 (0.47) |

TABLE 2-continued

Antimicrobial properties of the tested compounds against aerobic bacteria.

| | | Minimum inhibitory concentration (MIC), µg/ml (µM) | | | | |
|---|---|---|---|---|---|---|
| Entry | Compound | *Staphylococcus aureas* | *Enterococcus faecalis* | *Klebsiella pneumonia* | *Proteus vulgaris* | *Pseudomonas aeruginosa* |
| 8 | 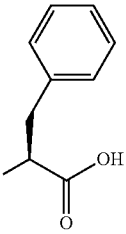<br>Molecular weight: 271.2760<br>PZA-Phe-OH | 64 (235.92) | 0.12 (0.44) | 64 (235.92) | 0.06 (0.22) | 0.12 (0.44) |
| 9 | 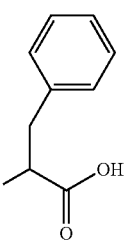<br>Molecular weight: 271.2760<br>PZA-DL-Phe-OH | 16 (58.98) | 0.03 (0.11) | 16 (58.98) | 0.06 (0.22) | 16 (58.98) |
| 10 | 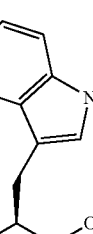<br>Molecular weight: 310.3130<br>PZA-Trp-OH | 64 (206.24) | 0.03 (0.10) | 64 (206.24) | 0.06 (0.19) | 0.12 (0.39) |
| 11 | 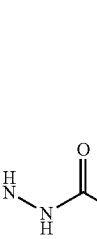<br>Molecular weight: 356.3860<br>PZA-Leu-INH | 2 (5.61) | 0.03 (0.08) | 4 (11.22) | 0.06 (0.17) | 64 (179.58) |

TABLE 2-continued

Antimicrobial properties of the tested compounds against aerobic bacteria.

| | | Minimum inhibitory concentration (MIC), μg/ml (μM) | | | | |
|---|---|---|---|---|---|---|
| Entry | Compound | Staphylococcus aureas | Enterococcus faecalis | Klebsiella pneumonia | Proteus vulgaris | Pseudomonas aeruginosa |
| 12 | 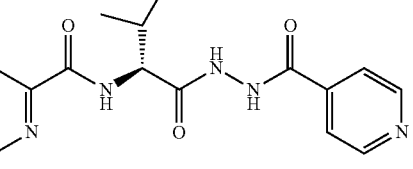 Molecular weight: 342.3590 PZA-Val-INH | 16 (46.73) | 0.12 (0.35) | 8 (23.37) | 0.06 (0.18) | 0.12 (0.35) |
| 13 | 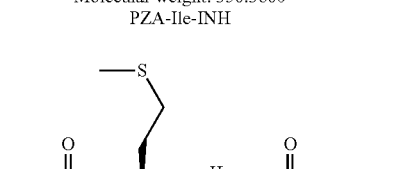 Molecular weight: 356.3860 PZA-Ile-INH | 16 (44.90) | 0.03 (0.08) | 8 (22.45) | 0.06 (0.17) | 0.12 (0.34) |
| 14 | 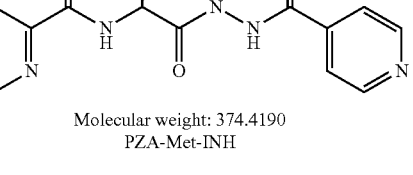 Molecular weight: 374.4190 PZA-Met-INH | 64 (170.93) | 0.03 (0.08) | 4 (10.68) | 0.06 (0.16) | 0.12 (0.32) |
| 15 | 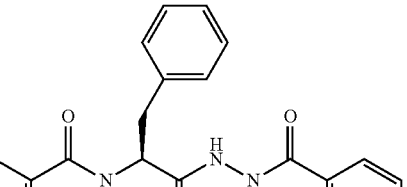 Molecular weight: 390.4030 PZA-Phe-INH | 16 (40.98) | 0.12 (0.31) | 8 (20.49) | 0.06 (0.15) | 0.12 (0.31) |
| 16 | 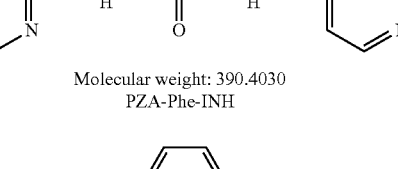 Molecular weight: 390.4030 PZA-DL-Phe-INH | 16 (40.98) | 0.03 (0.08) | 8 (20.49) | 16 (40.98) | 32 (81.97) |

TABLE 2-continued

Antimicrobial properties of the tested compounds against aerobic bacteria.

| | | Minimum inhibitory concentration (MIC), µg/ml (µM) | | | | |
|---|---|---|---|---|---|---|
| Entry | Compound | Staphylococcus aureas | Enterococcus faecalis | Klebsiella pneumonia | Proteus vulgaris | Pseudomonas aeruginosa |
| 17 | 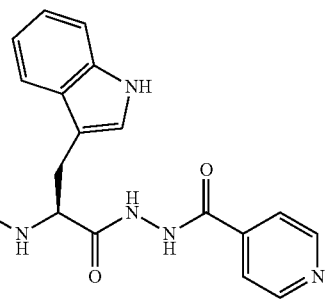<br>Molecular weight: 429.4400<br>PZA-Trp-INH | 16 (3726) | 0.03 (0.07) | 4 (9.31) | 0.06 (0.14) | 0.12 (0.28) |
| 18 | 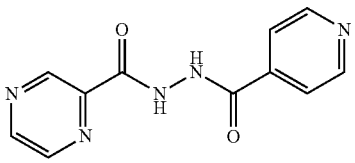<br>Molecular weight: 243.2260<br>PZA-INH | 8 (32.89) | 16 (65.78) | 8 (32.89) | 64 (263.13) | 0.03 (0.12) |
| 19 | 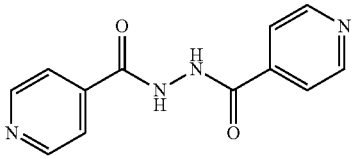<br>Molecular weight: 242.2380<br>Iso-INH | 4 (16.51) | 16 (66.05) | 4 (16.51) | 0.03 (0.12) | 0.06 (0.25) |

Example 3: Anti-Tuberculosis Properties

Results:

*Mycobacterium marinum:*

Some of the synthesized isonicotinic acid—pyrazinecarboxamide conjugates with amino acid linker reveal high anti-mycobacterial properties against *M. marinum* (about three folds potency; MIC=26.7, 25.6 mM of PZA-Met-INH and PZA-DL-Phe-INH, respectively) than the standard reference used (MIC=72.9 mM of INH). Other conjugates synthesized with potency comparable to that of the standard reference are also revealed (MIC=56.1, 58.4, 56.1, 51.2, 46.6, 41.1 mM for PZA-Leu-INH, PZA-Val-INH, PZA-Ile-INH, PZA-Phe-INH, PZA-Trp-INH, and PZA-INH, respectively). Compounds PZA, PZA-Leu-OH, PZA-DL-Phe-OH and Iso-INH show biological properties (MIC=81.2, 84.3, 73.7, 82.6 mM, respectively) close to that of the standard reference.

*Mycobacterium fortuitum:*

Compound PZA-DL-Phe-INH seems superior among all the synthesized analogs (MIC=25.6 mM) with a potency about 5.6 folds than that of the standard reference (MIC=145.8 mM of INH). 2. Many of the synthesized compounds (MIC=81.2, 84.3, 56.1, 58.4, 56.1, 53.4, 51.2, 46.6, 41.1, 82.6 mM PZA, PZA-Leu-OH, PZA-Leu-INH, PZA-Val-INH, PZA-Ile-INH, PZA-Met-INH, PZA-Phe-INH, PZA-Trp-INH, PZA-INH and Iso-INH, respectively) reveal high biological properties, about 2-3 folds than that of the standard reference.

*Mycobacterium bovis:*

Only compounds PZA-INH and Iso-INH (MIC=82.2, 82.6 mM, respectively) show promising antibacterial properties, about 1.8 folds lower than that of the standard reference (MIC=145.8 mM of INH). Pyrazine-2-carboxamide (MIC=162.4 mM) reveals antibacterial properties close to the standard reference.

TABLE 3

Anti-mycobacterial properties of the tested compounds.

| | | Minimum inhibitory concentration (MIC), mg/ml (mM) | | |
|---|---|---|---|---|
| Entry | Compound | Mycobacterium marinum | Mycobacterium fortuitum | Mycobacterium bovis |
| 1 | 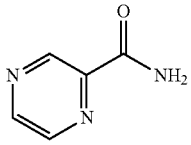<br>Molecular weight: 123.1150<br>Pyrazine-2-carboxamide<br>(pyrazinamide) | 10 (81.2) | 10 (81.2) | 20 (162.4) |
| 2 | 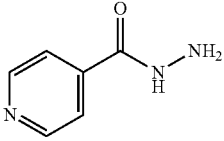<br>Molecular weight: 137.1420<br>Isoniazid | 10 (72.9) | 20 (145.8) | 20 (145.8) |
| 3 | 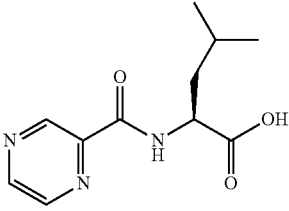<br>Molecular weight: 237.2590<br>PZA-Leu-OH | 20 (84.3) | 20 (84.3) | >20 (>84.3) |
| 4 | 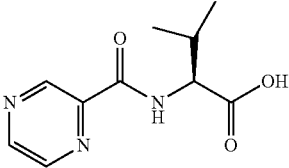<br>Molecular weight: 223.2320<br>PZA-Val-OH | >20 (>89.6) | >20 (>89.6) | >20 (>89.6) |
| 5 | 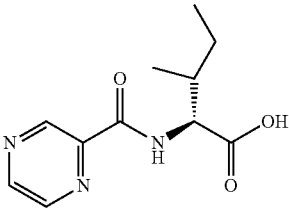<br>Molecular weight: 237.2590<br>PZA-Ile-OH | >20 (>84.3) | >20 (>84.3) | >20 (>84.3) |

TABLE 3-continued

Anti-mycobacterial properties of the tested compounds.

| | | Minimum inhibitory concentration (MIC), mg/ml (mM) | | |
| --- | --- | --- | --- | --- |
| Entry | Compound | *Mycobacterium marinum* | *Mycobacterium fortuitum* | *Mycobacterium bovis* |
| 6 | Molecular weight: 255.2920<br>PZA-Met-OH | >20 (>78.3) | >20 (>78.3) | >20 (>78.3) |
| 7 | Molecular weight: 271.2760<br>PZA-Phe-OH | >20 (>73.7) | >20 (>73.7) | >20 (>73.7) |
| 8 | Molecular weight: 271.2760<br>PZA-DL-Phe-OH | 20 (73.7) | >20 (>73.7) | >20 (>73.7) |
| 9 | Molecular weight: 310.3130<br>PZA-Trp-OH | >20 (>64.5) | >20 (>64.5) | >20 (>64.5) |

TABLE 3-continued

Anti-mycobacterial properties of the tested compounds.

| | | Minimum inhibitory concentration (MIC), mg/ml (mM) | | |
|---|---|---|---|---|
| Entry | Compound | Mycobacterium marinum | Mycobacterium fortuitum | Mycobacterium bovis |
| 10 | 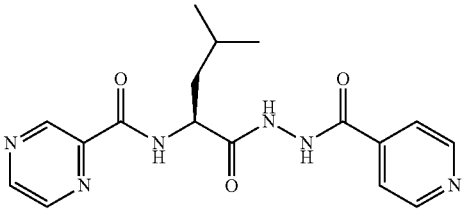<br>Molecular weight: 356.3860<br>PZA-Leu-INH | 20 (56.1) | 20 (56.1) | >20 (>56.1) |
| 11 | 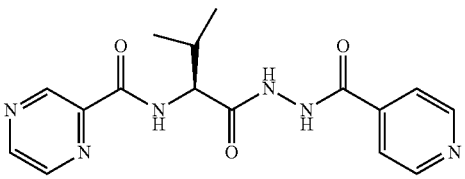<br>Molecular weight: 342.3590<br>PZA-Val-INH | 20 (58.4) | 20 (58.4) | >20 (>58.4) |
| 12 | 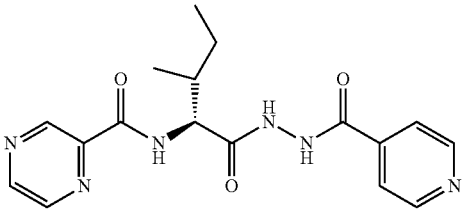<br>Molecular weight: 356.3860<br>PZA-Ile-INH | 20 (56.1) | 20 (56.1) | >20 (>56.1) |
| 13 | 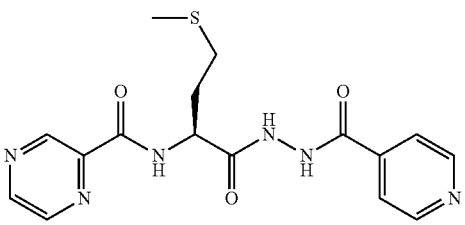<br>Molecular weight: 374.4190<br>PZA-Met-INH | 10 (26.7) | 20 (53.4) | >20 (>53.4) |
| 14 | 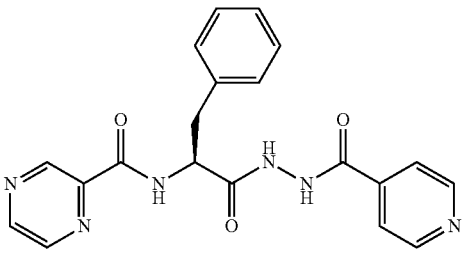<br>Molecular weight: 390.4030<br>PZA-Phe-INH | 20 (51.2) | 20 (51.2) | >20 (>51.2) |

TABLE 3-continued

Anti-mycobacterial properties of the tested compounds.

| Entry | Compound | Minimum inhibitory concentration (MIC), mg/ml (mM) | | |
|---|---|---|---|---|
| | | *Mycobacterium marinum* | *Mycobacterium fortuitum* | *Mycobacterium bovis* |
| 15 | 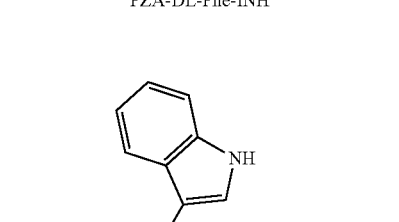<br>Molecular weight: 390.4030<br>PZA-DL-Phe-INH | 10 (25.6) | 10 (25.6) | >20 (>51.2) |
| 16 | 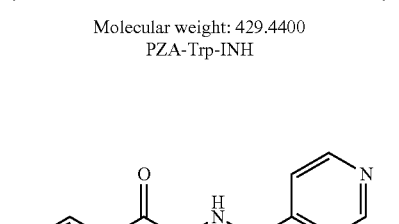<br>Molecular weight: 429.4400<br>PZA-Trp-INH | 20 (46.6) | 20 (46.6) | >20 (>46.6) |
| 17 | 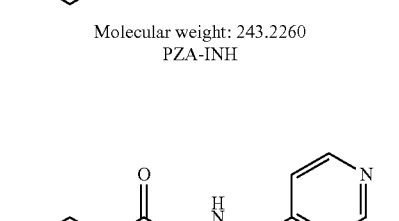<br>Molecular weight: 243.2260<br>PZA-INH | 10 (41.1) | 10 (41.1) | 20 (82.2) |
| 18 | 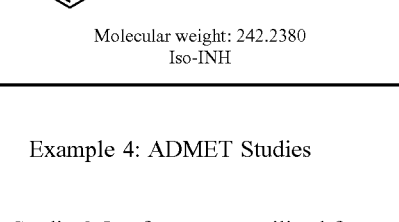<br>Molecular weight: 242.2380<br>Iso-INH | 20 (82.6) | 20 (82.6) | 20 (82.6) |

Example 4: ADMET Studies

Methods

Discovery Studio 2.5 software was utilized for computational ADMET (absorption, distribution, metabolism, excretion, toxicity) studies. From the results obtained it has been noticed that most of the tested compounds show optimal aqueous solubility and good to moderate intestinal absorption. Blood-brain barrier penetration (BBB) is ranging from low to very low level. Many of the tested compounds show non-hepatotoxicity (Table 4). These computational observations indicate that many of the constructed compounds are good hits to be handled by more sophisticated biological/pharmacological studies for optimizing promising bio-active agents.

TABLE 4
ADMET descriptor values for the tested compounds.
| Entry | Compound | Aqueous solubility [a] | Intestinal absorption [b] | BBB [c] | PPB [d] | Hepatotoxicity [e] |
|---|---|---|---|---|---|---|
| 1 | 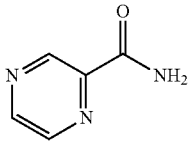  Molecular weight: 123.1150  Pyrazine-2-carboxamide (PZA) | 5 | 1 | 3 | 0 | 1 |
| 2 | 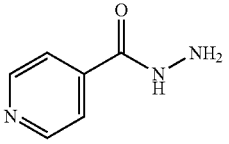  Molecular weight: 137.1420  INH | 4 | 0 | 3 | 1 | 0 |
| 3 | 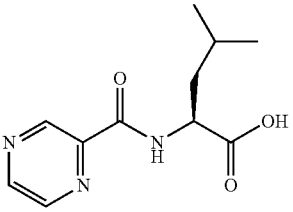  Molecular weight: 237.2590  PZA-Leu-OH | 4 | 0 | 3 | 0 | 0 |
| 4 | 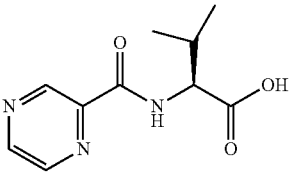  Molecular weight: 223.2320  PZA-Val-OH | 4 | 0 | 3 | 0 | 0 |
| 5 | 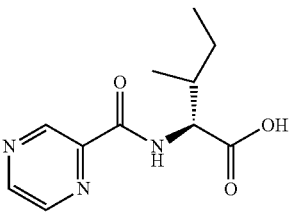  Molecular weight: 237.2590  PZA-Ile-OH | 4 | 0 | 3 | 0 | 0 |
| 6 | 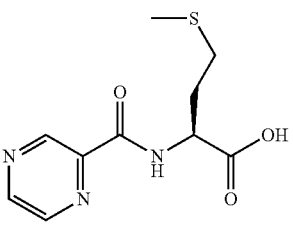  Molecular weight: 255.2920  PZA-Met-OH | 4 | 0 | 3 | 0 | 0 |

TABLE 4-continued
ADMET descriptor values for the tested compounds.
| Entry | Compound | Aqueous solubility[a] | Intestinal absorption[b] | BBB[c] | PPB[d] | Hepatotoxicity[e] |
|---|---|---|---|---|---|---|
| 7 | 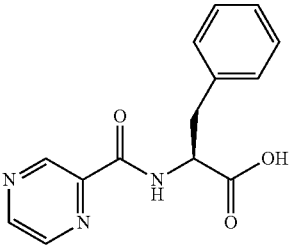  Molecular weight: 271.2760  PZA-Phe-OH | 4 | 0 | 3 | 2 | 1 |
| 8 | 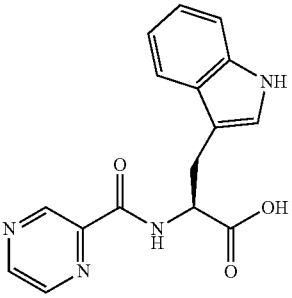  Molecular weight: 310.3130  PZA-Trp-OH | 3 | 0 | 3 | 2 | 1 |
| 9 | 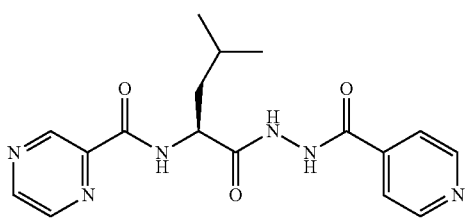  Molecular weight: 356.3860  PZA-Leu-INH | 4 | 1 | 4 | 0 | 0 |
| 10 | 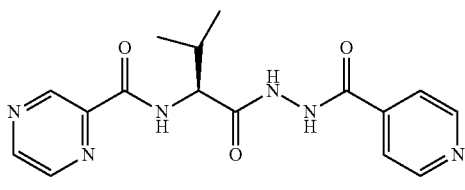  Molecular weight: 342.3590  PZA-Val-INH | 4 | 1 | 4 | 0 | 1 |
| 11 | 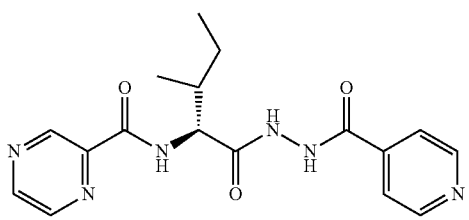  Molecular weight: 356.3860  PZA-Ile-INH | 4 | 1 | 4 | 0 | 0 |

TABLE 4-continued

ADMET descriptor values for the tested compounds.

| Entry | Compound | Aqueous solubility[a] | Intestinal absorption[b] | BBB[c] | PPB[d] | Hepatotoxicity[e] |
|---|---|---|---|---|---|---|
| 12 | Molecular weight: 374.4190<br>PZA-Met-INH | 4 | 1 | 4 | 1 | 0 |
| 13 | Molecular weight: 390.4030<br>PZA-Phe-INH | 4 | 1 | 4 | 2 | 1 |
| 14 | Molecular weight: 429.4400<br>PZA-Trp-INH | 3 | 1 | 4 | 2 | 1 |
| 15 | Molecular weight: 243.2260<br>PZA-INH | 4 | 0 | 4 | 2 | 1 |
| 16 | Molecular weight: 242.2380<br>Iso-INH | 4 | 0 | 3 | 2 | 1 |

[a] Aqueous solubility level: 0, extremely low; 1, very low; 2, low; 3, good; 4, optimal; 5, too soluble; 6, unknown.
[b] Intestinal absorption level: 0, good; 1, moderate; 2, poor; 3 very poor.
[c] Blood brain barrier penetration (BBB) level: 0, very good; 1, high; 2, medium; 3, low; 4, very low.
[d] Plasma protein binding (PPB) level: 0, <90%; 1, >90%; 2, >95%.
[e] Hepatotoxicity level: 0, non-toxic; 1, toxic.

Example 5: 2D-QSAR

Results:

*Mycobacterium marinum*

The two-descriptor model was determined to describe the bio-properties of the biologically active agents against *Mycobacterium marinum* (Table 4

TABLE 6-continued
Observed and estimated MIC values for the tested compounds against *Mycobacterium marinum* according to the BMLR-QSAR model.
| Entry | Compound | Observed MIC, mM | Estimated MIC, mM | Error[a] |
|---|---|---|---|---|
| 3 | 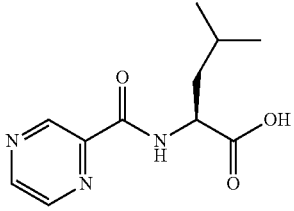 PZA-Leu-OH | 84.3 | 79.8 | 4.5 |
| 4 | 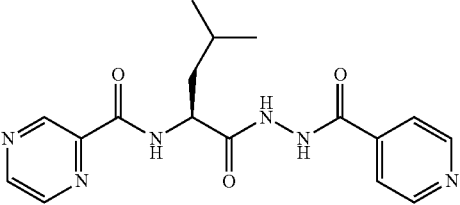 PZA-Leu-INH | 56.1 | 46.7 | 9.4 |
| 5 | 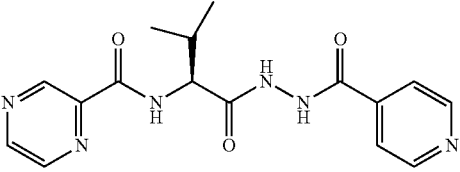 PZA-Val-INH | 58.4 | 57.4 | 1.0 |
| 6 | 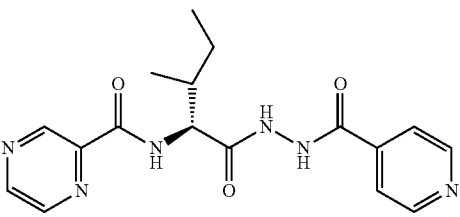 PZA-Ile-INH | 56.1 | 52.5 | 3.6 |
| 7 | 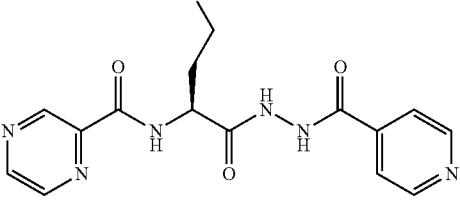 PZA-Met-INH | 26.7 | 30.8 | −4.1 |

TABLE 6-continued

Observed and estimated MIC values for the tested compounds against *Mycobacterium marinum* according to the BMLR-QSAR model.

| Entry | Compound | Observed MIC, mM | Estimated MIC, mM | Error[a] |
|---|---|---|---|---|
| 8 | 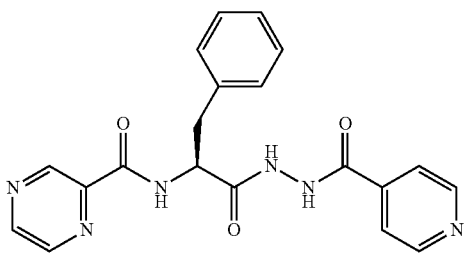 PZA-Phe-INH | 51.2 | 46.3 | 4.9 |
| 9 | 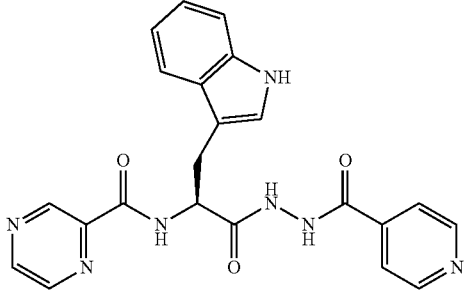 PZA-Trp-INH | 46.6 | 44.8 | 1.8 |
| 10 | 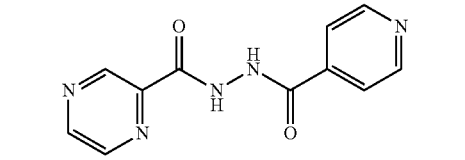 PZA-INH | 41.1 | 48.0 | −6.9 |
| 11 | 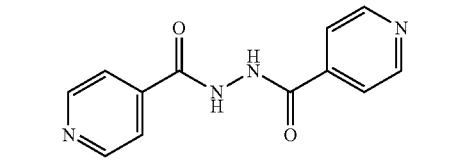 Iso-INH | 82.6 | 82.3 | 0.3 |

[a]Error is the difference between the observed and estimated biologically activity (MIC) value.

TABLE 7

Molecular descriptor values of the BMLR-QSAR model for the tested compounds against *Mycobacterium marinum* according to the BMLR-QSAR model.

| Entry | Compound | Descriptors[a] $D_1$ | $D_2$ |
|---|---|---|---|
| 1 | PZA | 330.1631 | 127.8817 |
| 2 | INH | 329.9877 | 128.4424 |
| 3 | PZA-Leu-OH | 330.4742 | 127.7163 |
| 4 | PZA-Leu-INH | 330.664 | 129.4675 |
| 5 | PZA-Val-INH | 330.6187 | 128.7496 |
| 6 | PZA-Ile-INH | 330.4774 | 129.3105 |
| 7 | PZA-Met-INH | 330.7008 | 131.0057 |
| 8 | PZA-Phe-INH | 330.426 | 129.8765 |
| 9 | PZA-Trp-INH | 330.3036 | 130.193 |
| 10 | PZA-INH | 330.8481 | 129.0796 |
| 11 | Iso-INH | 329.2578 | 129.4907 |

[a] $D_1$ = Max. e-n attraction for bond C—N, $D_2$ = Max. e-e repulsion for bond C—C.

TABLE 8

The descriptor of the BMLR-QSAR model for the tested compounds against *Mycobacterium fortuitum*.

| Entry | ID | Coefficient | s | t | Descriptor |
|---|---|---|---|---|---|
| 1 | 0 | −2.6795 | 0.388 | −6.913 | Intercept |
| 2 | $D_1$ | 0.0298467 | 0.003 | 11.054 | Max. e-e repulsion for atom N |
| 3 | $D_2$ | 80.0736 | 3.734 | 21.444 | Avg. electroph. react. index for atom N |

N =11, n = 2, $R^2$ = 0.984, $R^2cvOO$ = 0.962, $R^2cvMO$ = 0.972, F = 240.314, $s^2$ = 0.001
Log(MIC, mM) = −2.6795 + (0.0298467 × $D_1$) − (80.0736 × $D_2$)

TABLE 9

Observed and estimated MIC values for the tested compounds against *Mycobacterium fortuitum*

| Entry | Compound | Observed MIC, mM | Estimated MIC, mM | Error[a] |
|---|---|---|---|---|
| 1 | Pyrazine-2-carboxamide (PZA) | 81.2 | 78.4 | 2.8 |
| 2 | INH | 145.8 | 152.9 | −7.1 |
| 3 | PZA-Leu-OH | 84.3 | 81.5 | 2.8 |
| 4 | PZA-Leu-INH | 56.1 | 54.3 | 1.8 |
| 5 | PZA-Val-INH | 58.4 | 55.9 | 2.5 |

TABLE 9-continued

Observed and estimated MIC values for the tested compounds against *Mycobacterium fortuitum*

| Entry | Compound | Observed MIC, mM | Estimated MIC, mM | Error[a] |
|---|---|---|---|---|
| 6 | PZA-Ile-INH | 56.1 | 54.0 | 2.1 |
| 7 | PZA-Met-INH | 53.4 | 57.9 | -4.5 |
| 8 | PZA-Phe-INH | 51.2 | 53.6 | -2.4 |
| 9 | PZA-Trp-INH | 46.6 | 48.2 | -1.6 |
| 10 | PZA-INH | 41.1 | 42.0 | -0.9 |

TABLE 9-continued

Observed and estimated MIC values for the tested compounds against *Mycobacterium fortuitum*

| Entry | Compound | Observed MIC, mM | Estimated MIC, mM | Error[a] |
|---|---|---|---|---|
| 11 | Iso-INH | 82.6 | 79.0 | 3.6 |

[a]Error is the difference between the observed and estimated biologically activity (MIC) values.

TABLE 10

Molecular descriptor values of the BMLR-QSAR model for the tested compounds against *Mycobacterium fortuitum* according to the BMLR-QSAR model.

| | | Descriptors [a] | |
|---|---|---|---|
| Entry | Compound | $D_1$ | $D_2$ |
| 1 | PZA | 147.356 | 0.00219 |
| 2 | INH | 142.5146 | 0.00762 |
| 3 | PZA-Leu-OH | 142.6322 | 0.00416 |
| 4 | PZA-Leu-INH | 142.502 | 0.00201 |
| 5 | PZA-Val-INH | 142.4075 | 0.00221 |
| 6 | PZA-Ile-INH | 142.064 | 0.00215 |
| 7 | PZA-Met-INH | 142.7317 | 0.00227 |
| 8 | PZA-Phe-INH | 142.3404 | 0.002 |
| 9 | PZA-Trp-INH | 144.0619 | 0.00078 |
| 10 | PZA-INH | 137.0116 | 0.00266 |
| 11 | Iso-INH | 137.8948 | 0.00576 |

[a] $D_1$ = Max. e-e repulsion for atom N, $D_2$ = Avg. electroph. react. index for atom N.

Example 6: 3D-Pharmacophore Modeling

Methods:

3D-Pharmacophore modeling is an important computational technique explains the biological/pharmacological properties of compound(s) through alignment of the structural elements with chemical features in 3D-array. The biologically active compounds were undertaken by Discovery Studio 2.5 software searching for the 3D-pharmacophoric modeling in which alignment of the synthesized conjugates describes the observed biological properties.

Results:

*Mycobacterium marinum*

Figure 7A:
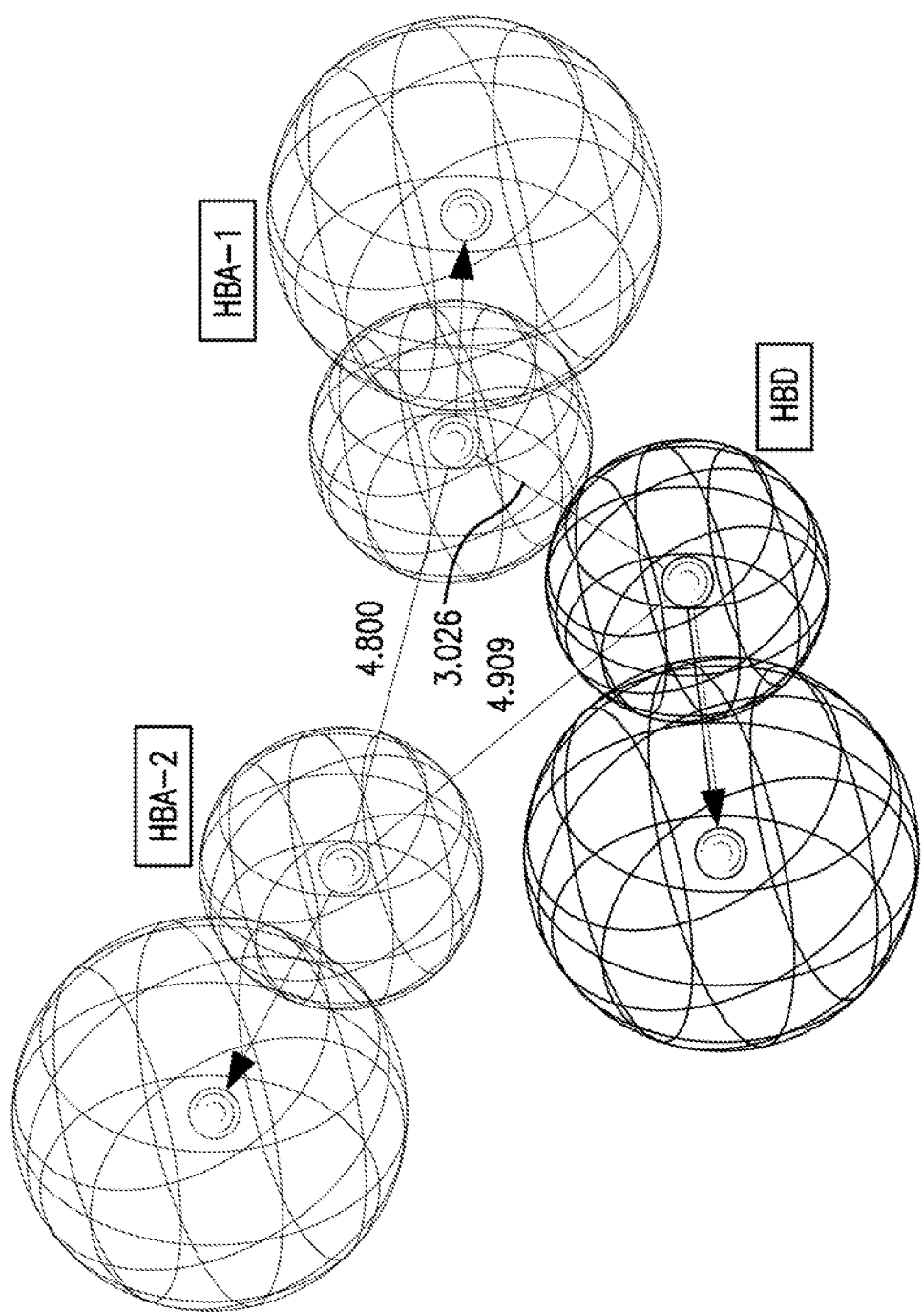
Figure 8A:
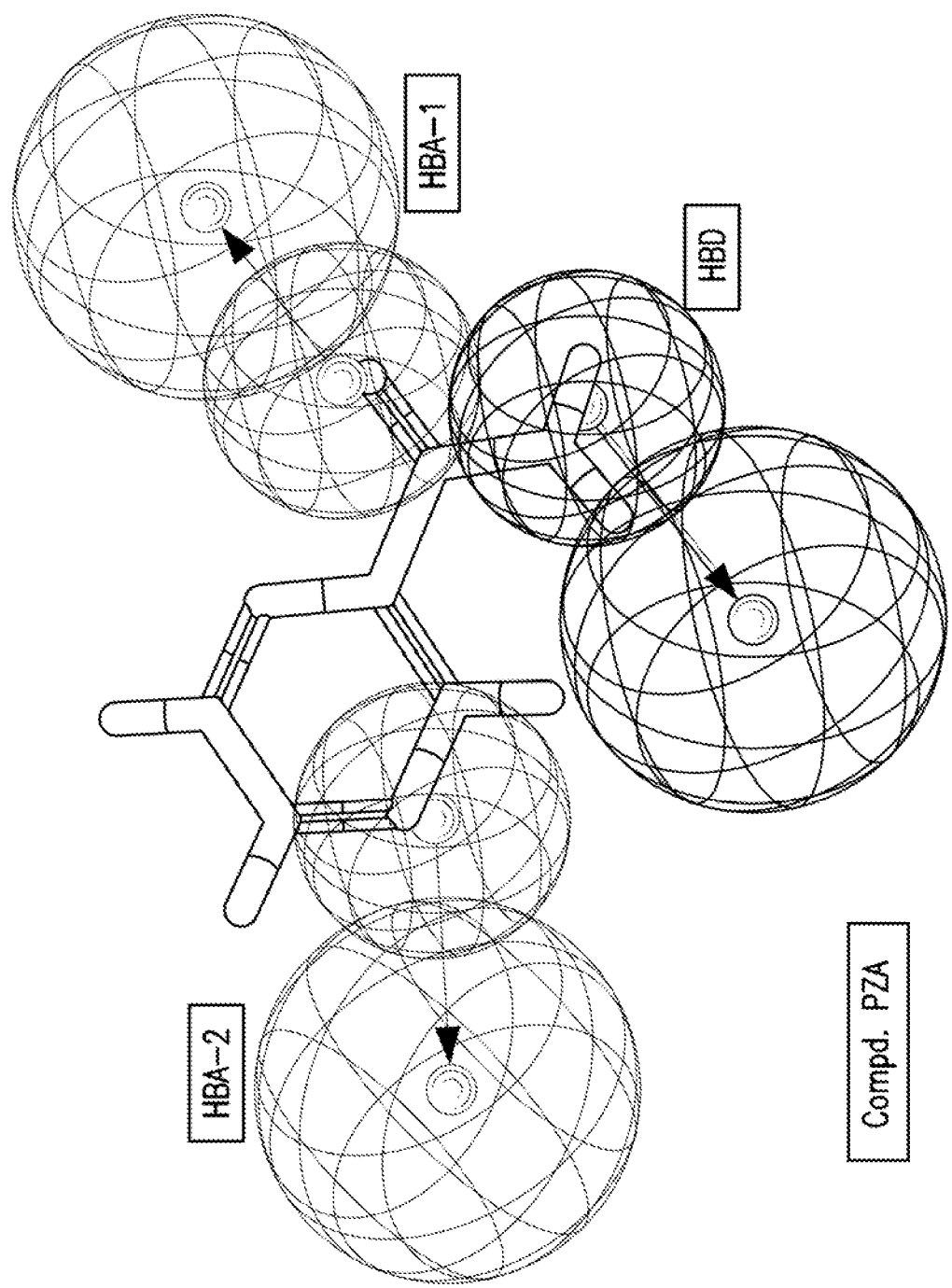
Figure 8B:
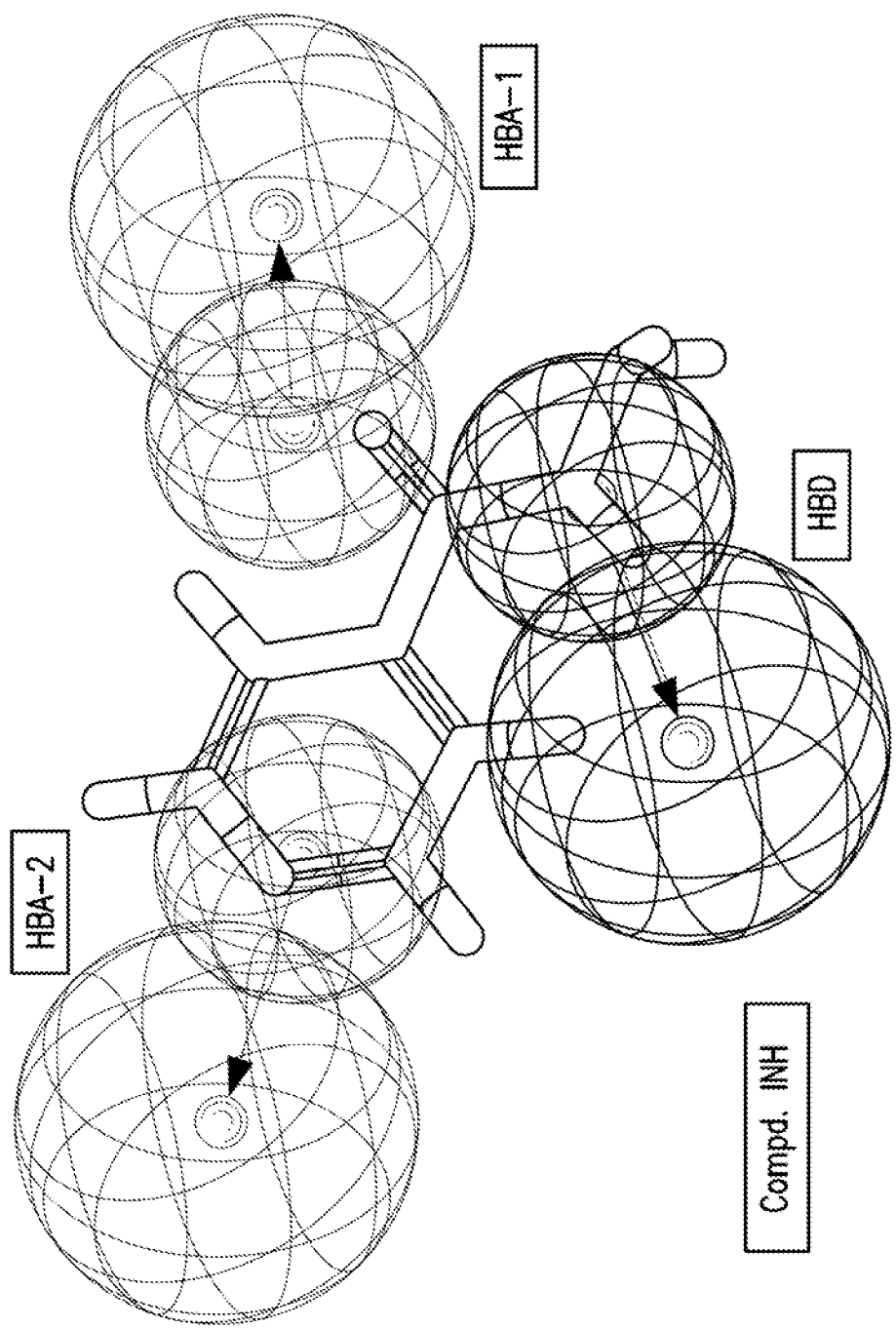
Figure 8C:
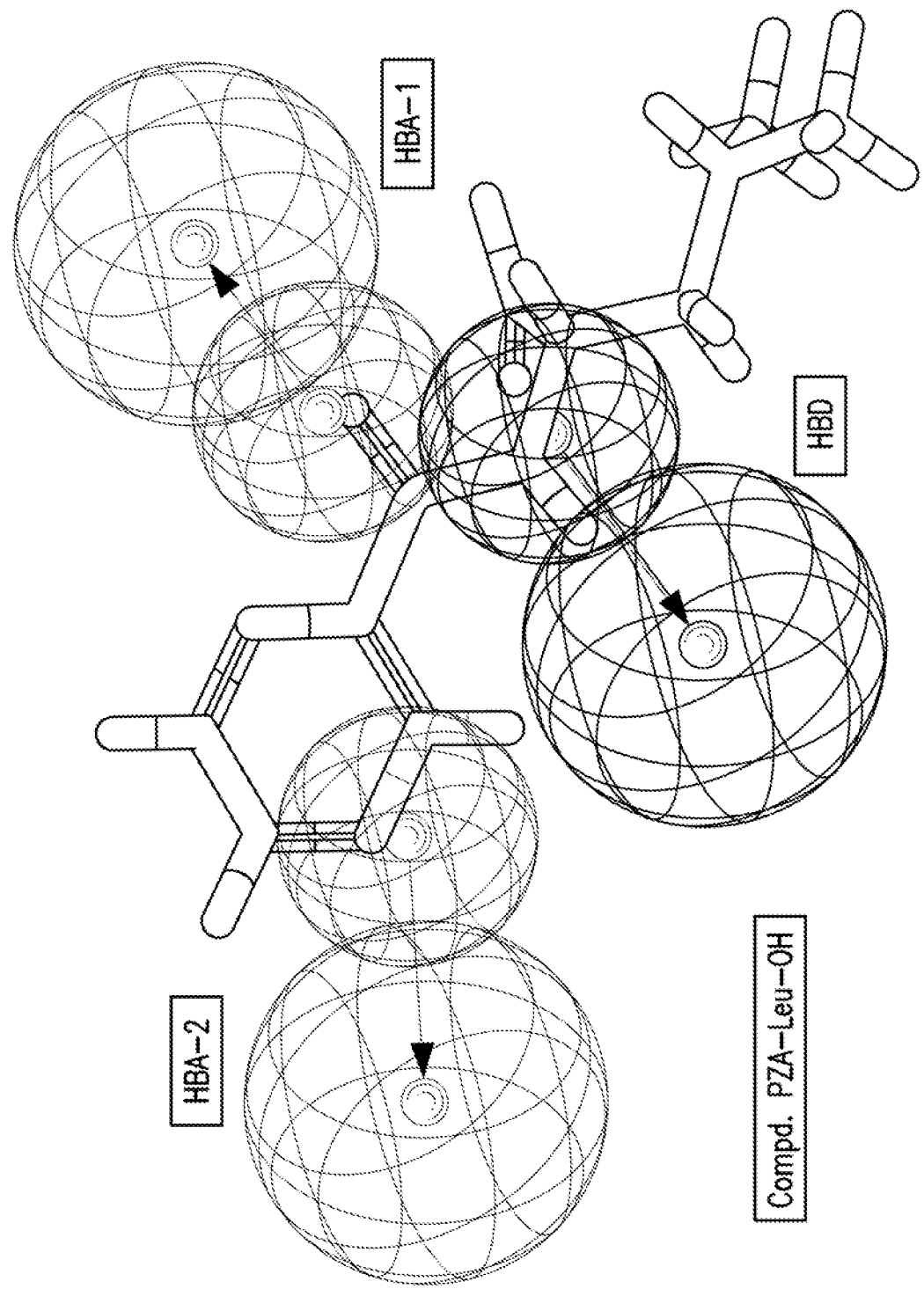
Figure 8D:
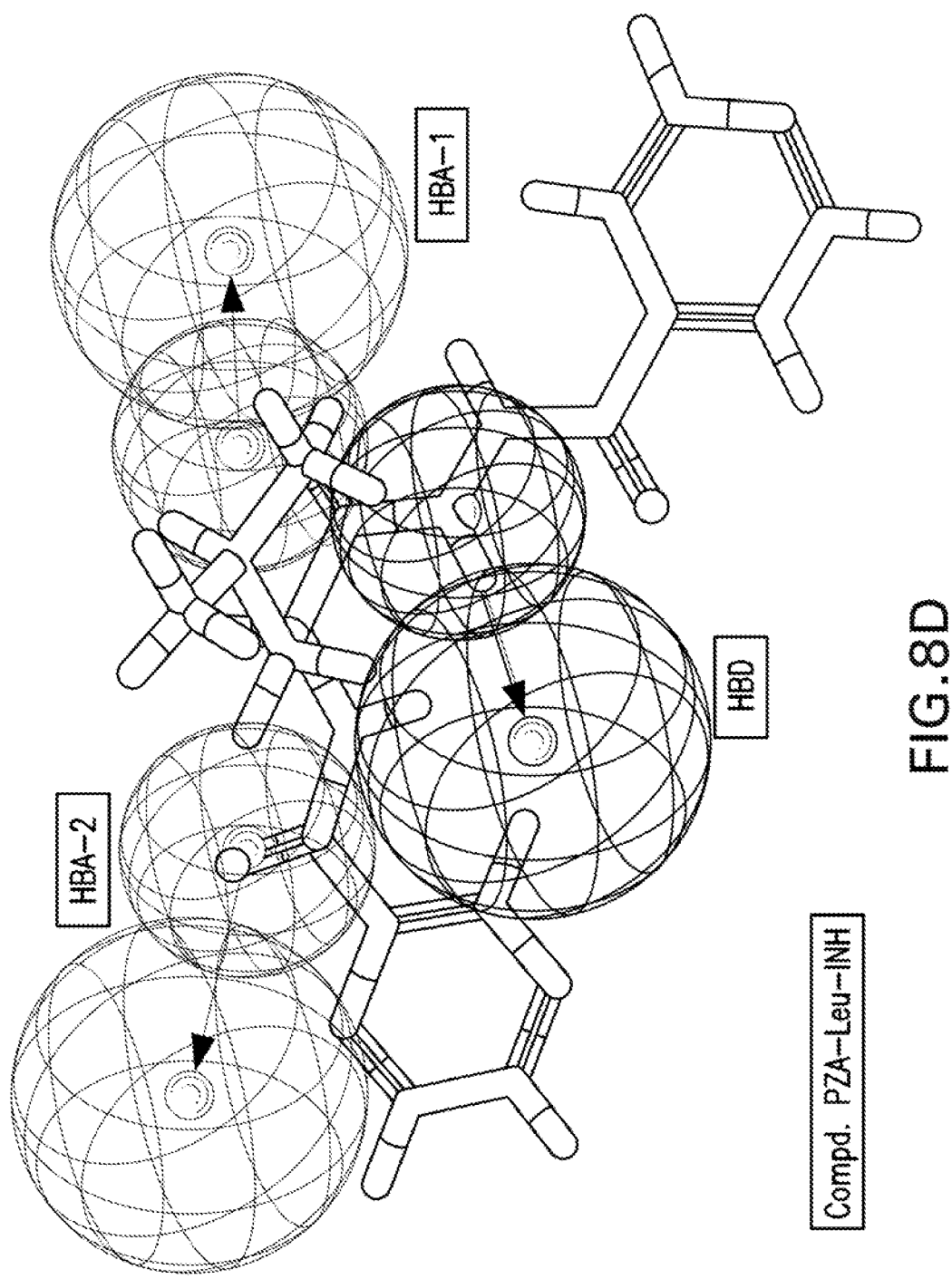
Figure 8E:
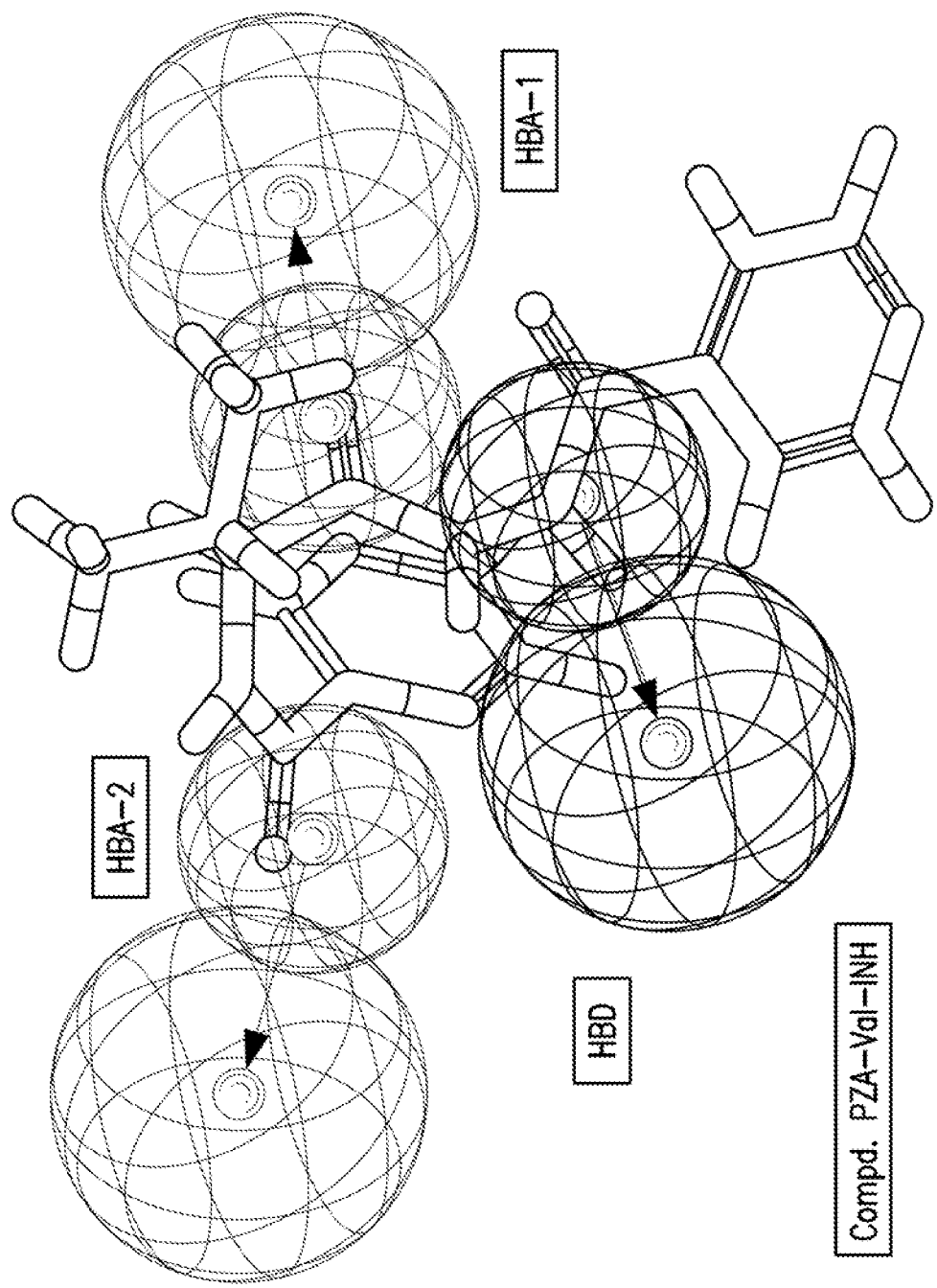
Figure 8F:
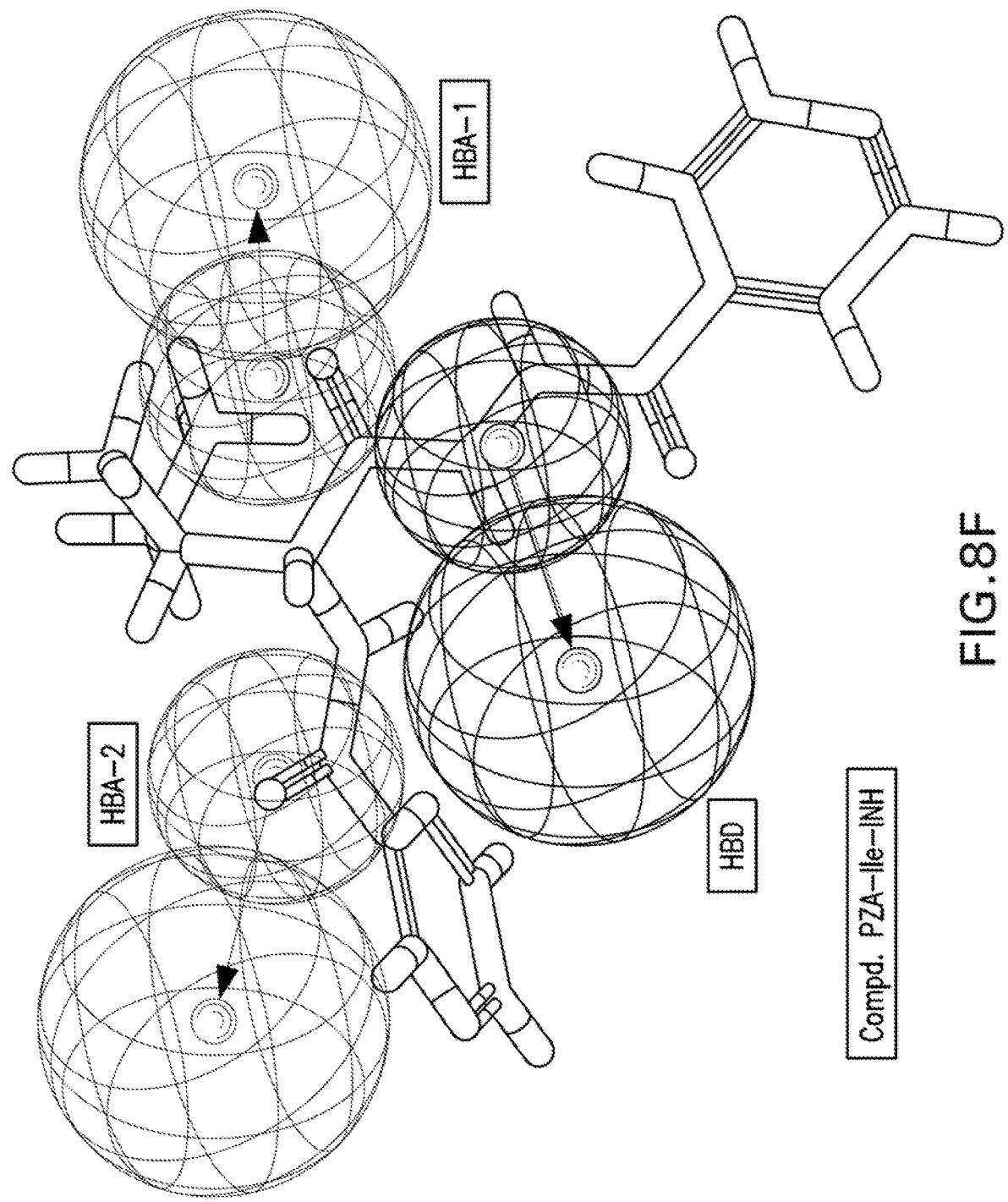
Figure 8G:
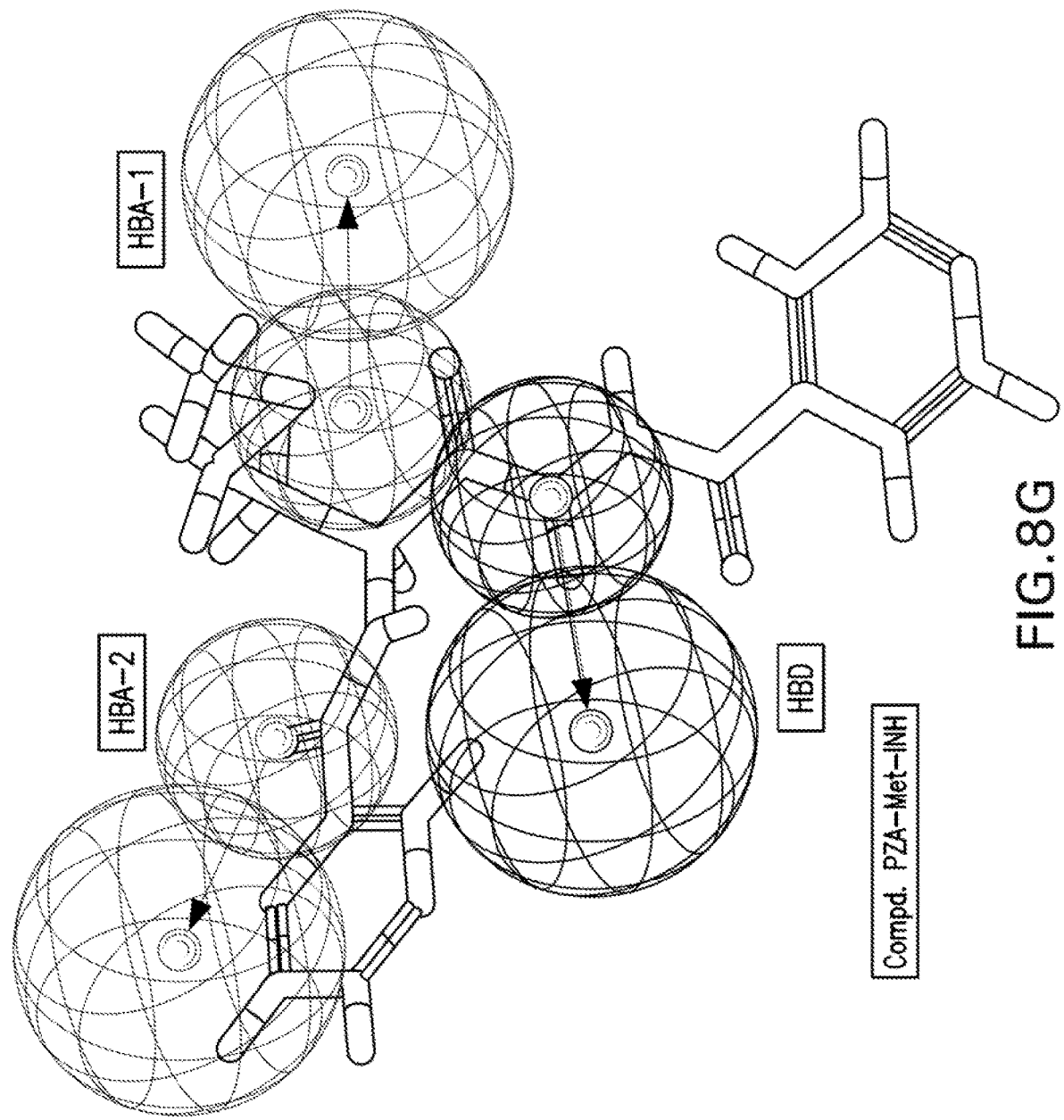
Figure 8H:
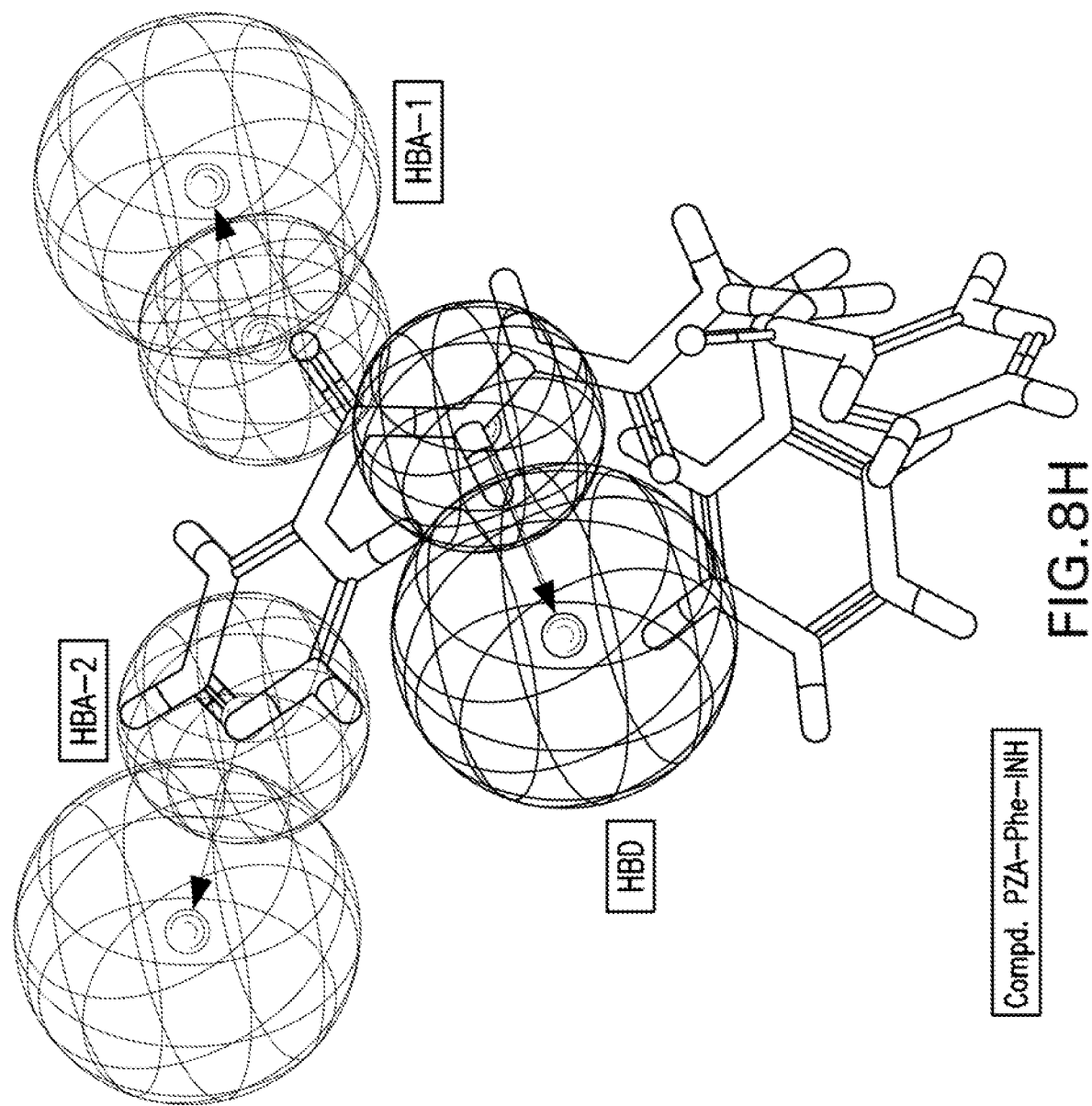
Figure 81:
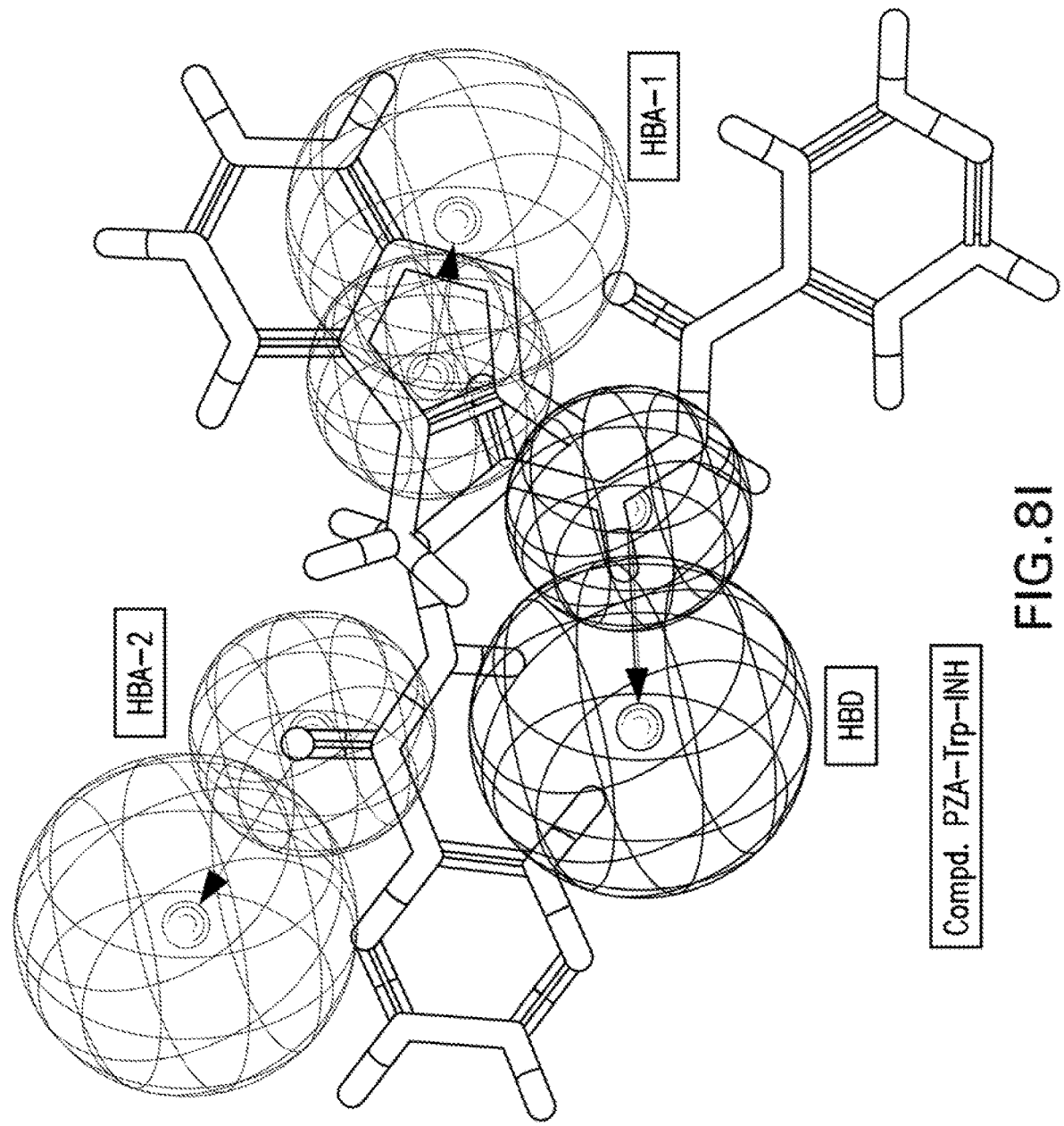
Figure 8J:
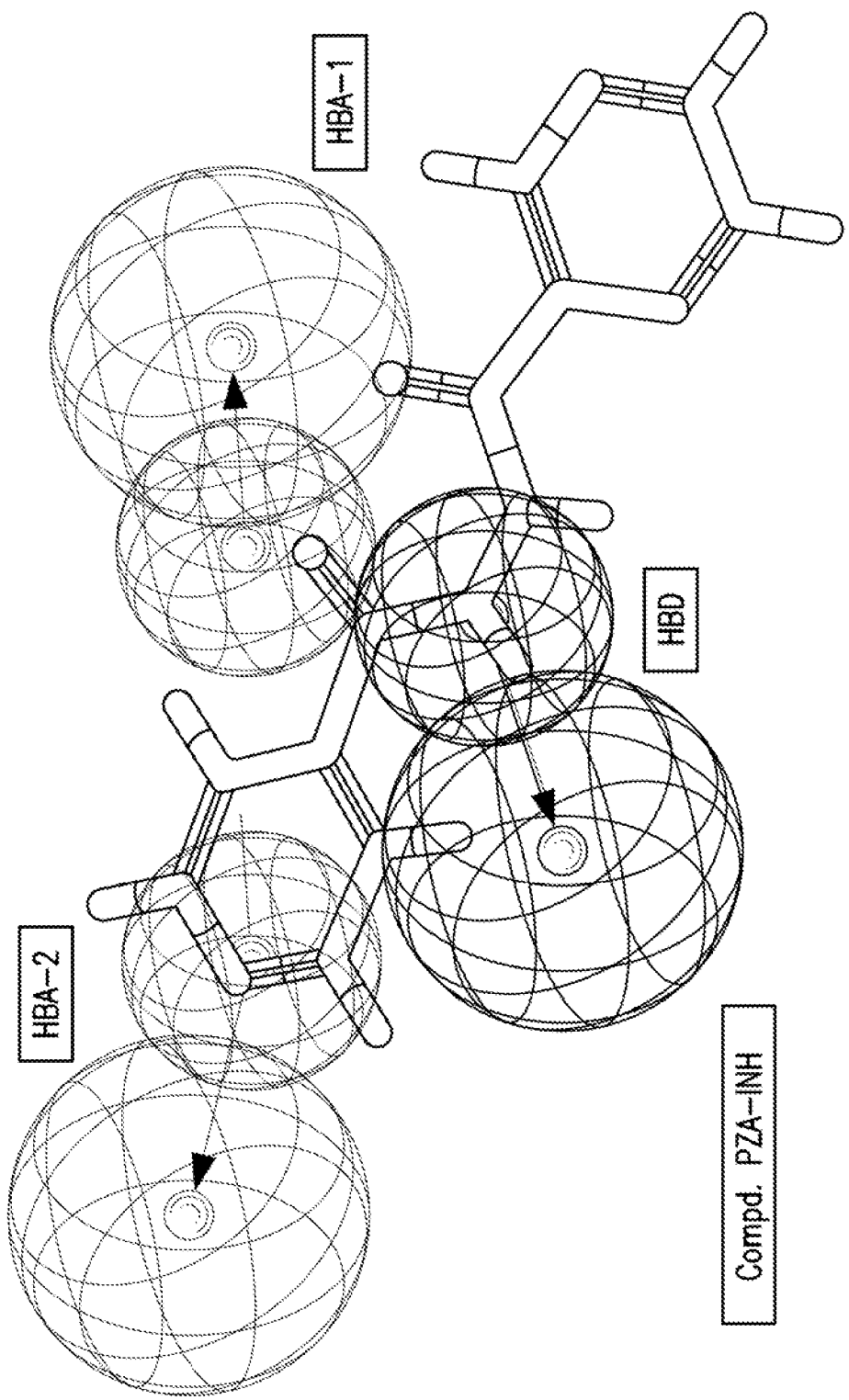
Figure 8K:
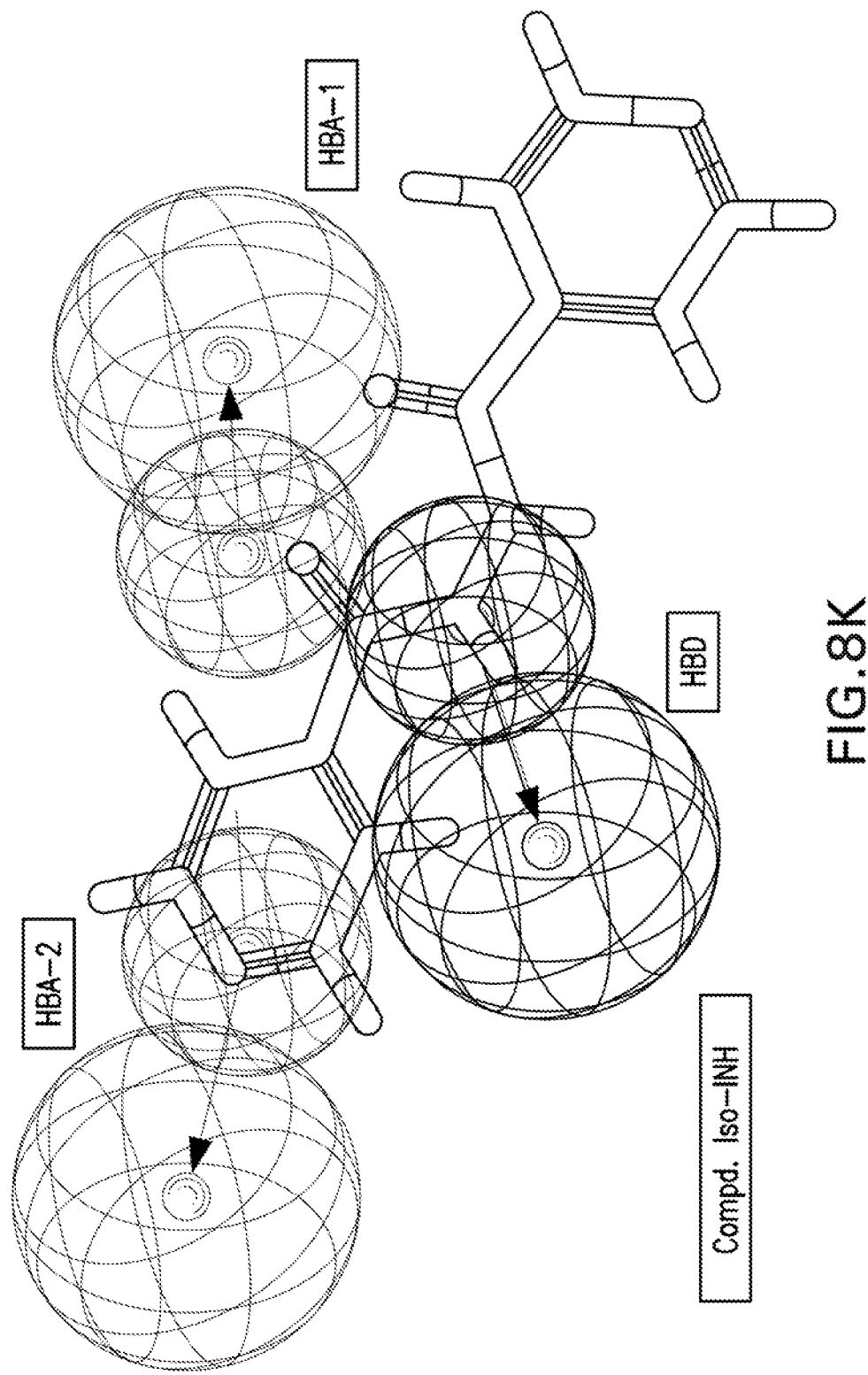

3D-pharmacophoric modeling of the biologically active compounds against *Mycobacterium marinum* reveals 3D-array of three chemical features [two hydrogen bonding acceptors (HBA-1, HBA-2) and one hydrogen bonding donor (HBD)] (FIGS. 7A-7B). Table 11 exhibits the estimated/predicted properties of the tested compounds due to alignment in the 3D-pharmacophore. From the observed data, it has been noticed that the N-2 of isonicotinic acid hydrazide is aligned with the pharmacophoric HBD in compounds PZA-Met-INH and PZA-Trp-INH, which are the most effective agents synthesized against M. marinum ($MIC_{observed}$= 26.7, 46.6; $MIC_{estimated}$=33.4, 38.1 mM for PZA-Met-INH and PZA-Trp-INH, respectively). However, slight displacement is observed for compounds PZA-Leu-INH, PZA-Val-INH and PZA-Phe-INH which are also promising agents relative to the standard reference used (INH where, the N-1 of isonicotinic acid hydrazide of these compounds is aligned with the pharmacophoric HBD ($MIC_{observed}$=56.1, 58.4, 51.2; $MIC_{estimated}$=46.9, 43.7, 39.3 mM for PZA-Leu-INH, PZA-Val-INH, and PZA-Phe-INH, respectively). Generally, estimated properties of the tested compounds are correlated with the observed observations and among each other preserving their potencies (FIGS. 8A-8K).

*Mycobacterium fortuitum*

Figure 9A:
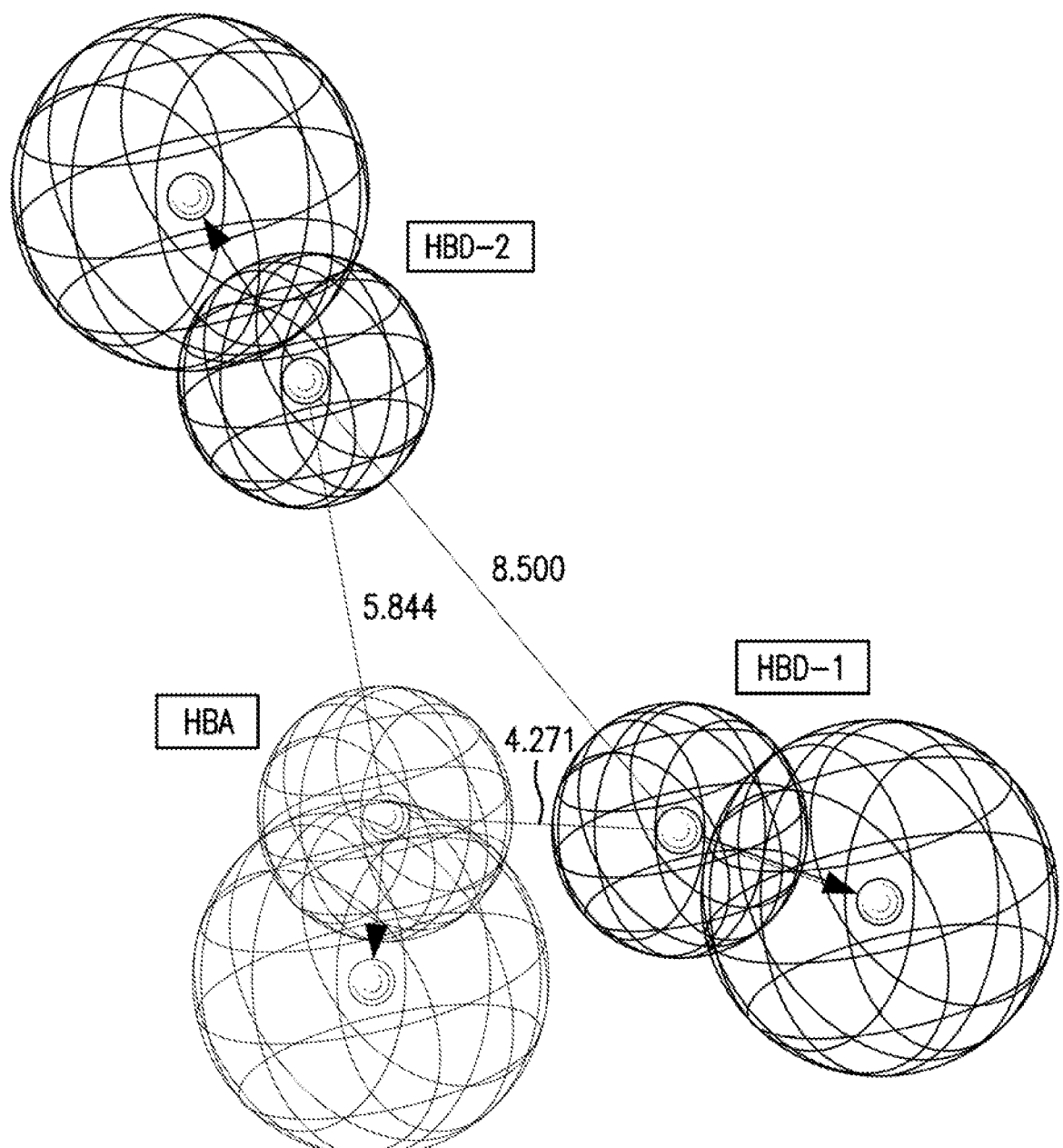
FIGS. 9A-9B are illustrations showing constraint distances (FIG. 9A; HBD-1–HBD-2=8.500, HBD-1–HBA=4.271, HBD-2–HBA=5.844 Å) and constraint angles (FIG. 9B; HBD-1–HBD-2–HBA=27.45°) of the generated 3D-pharmacophore for the synthesized bio-active compounds against *Mycobacterium fortuitum* which contains two hydrogen bonding donors (HBD-1, HBD-2) and one hydrogen bonding acceptor (HBA).
Figure 9B:
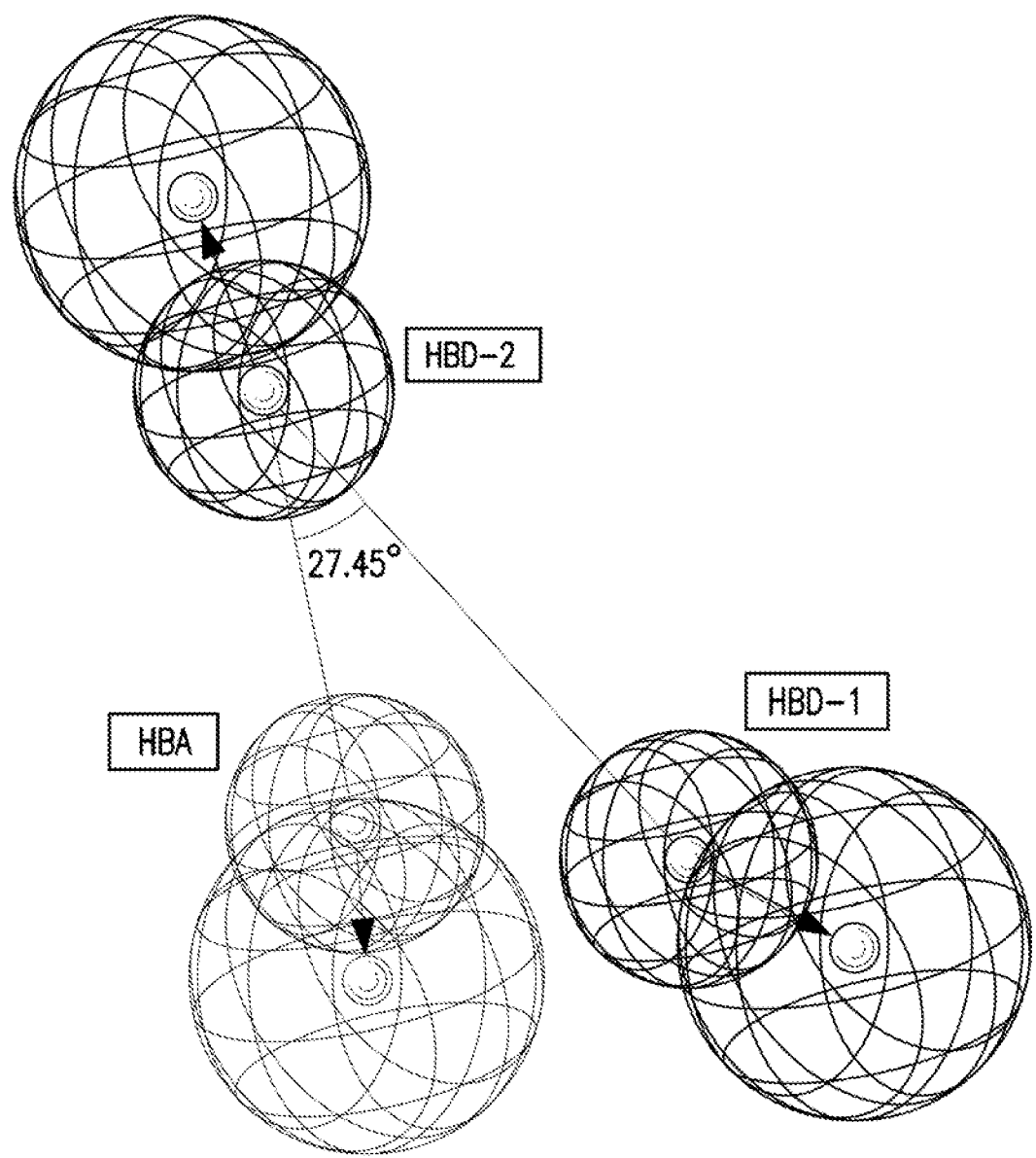
Figure 10A:
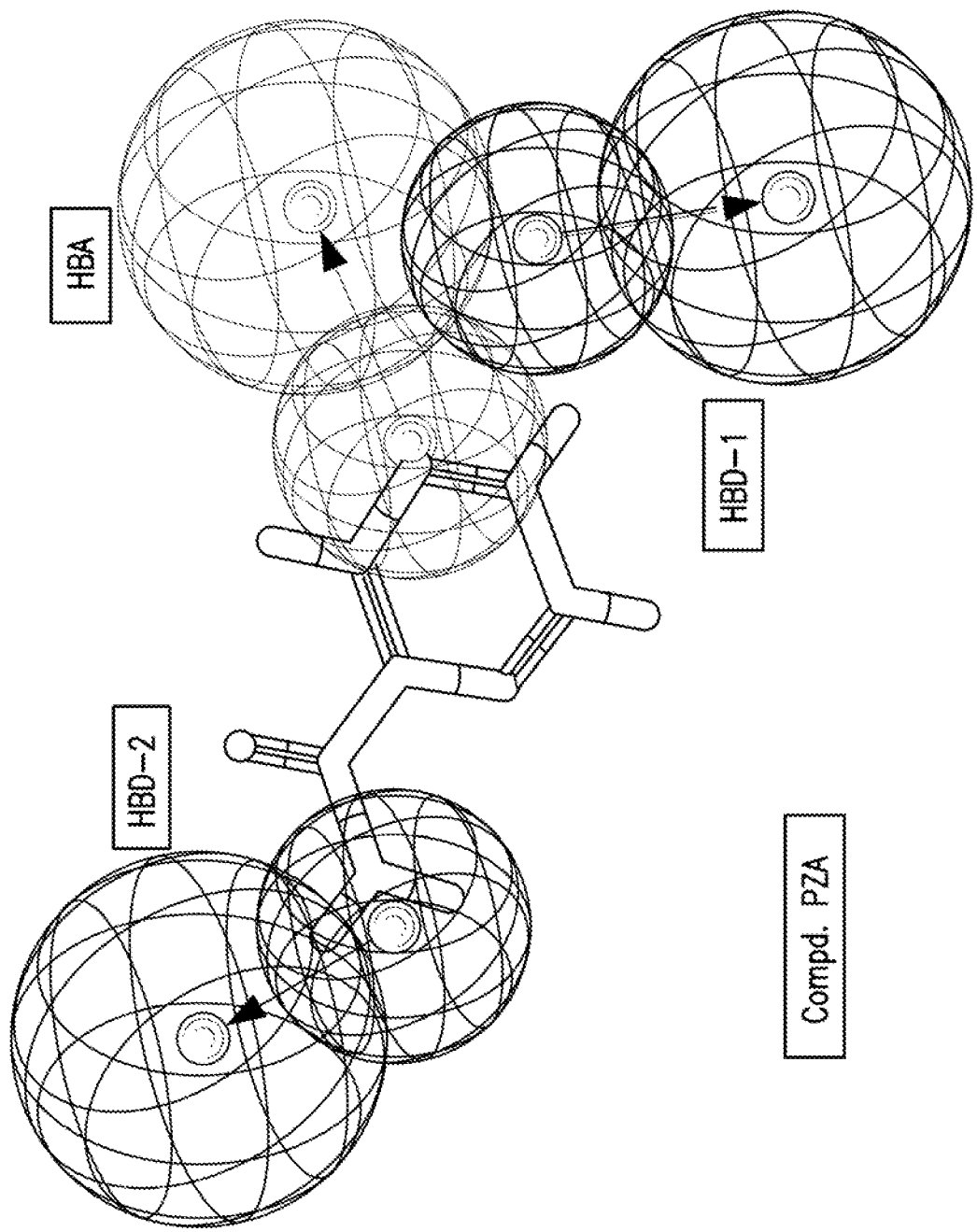
Figure 10B:
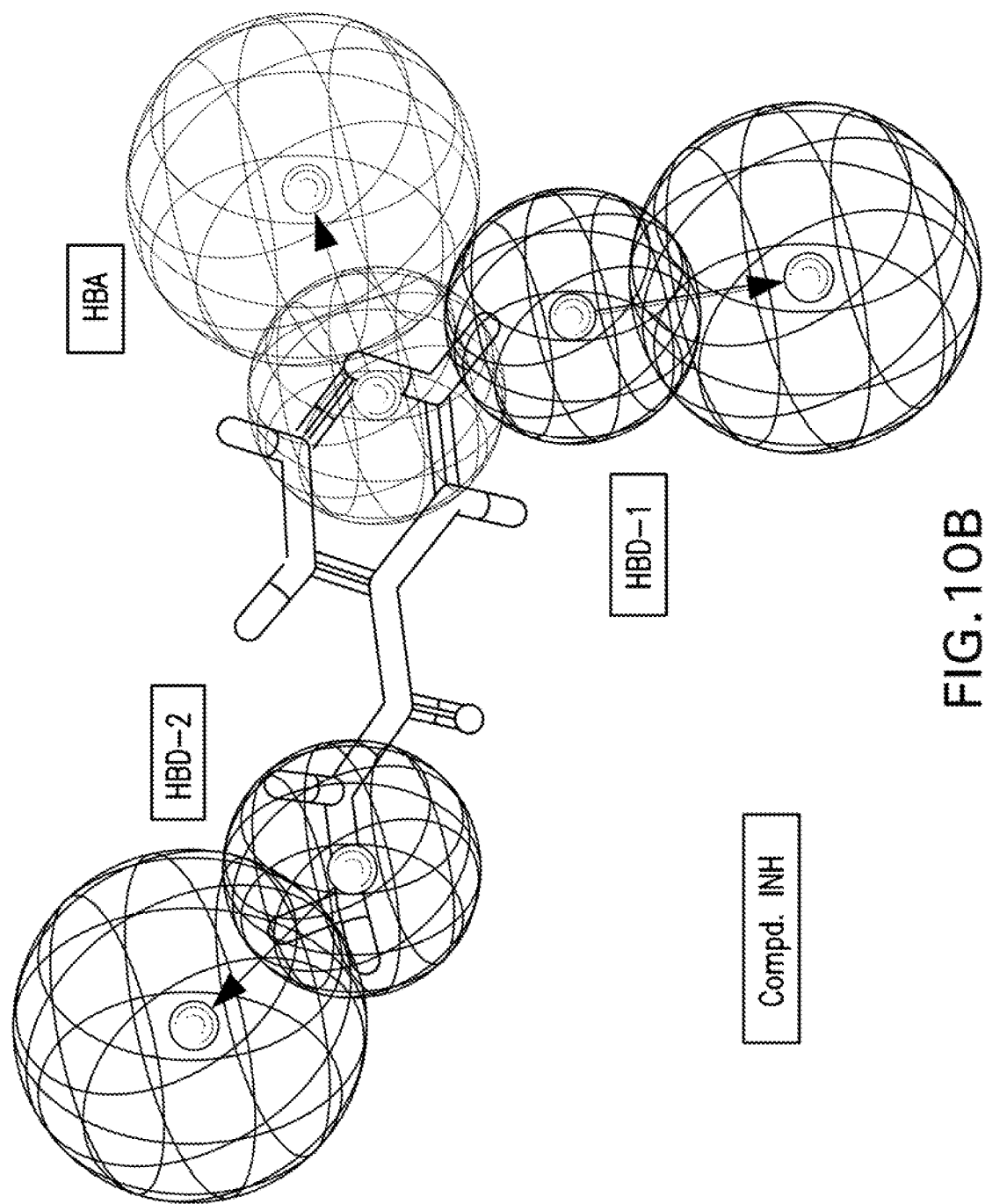
Figure 10C:
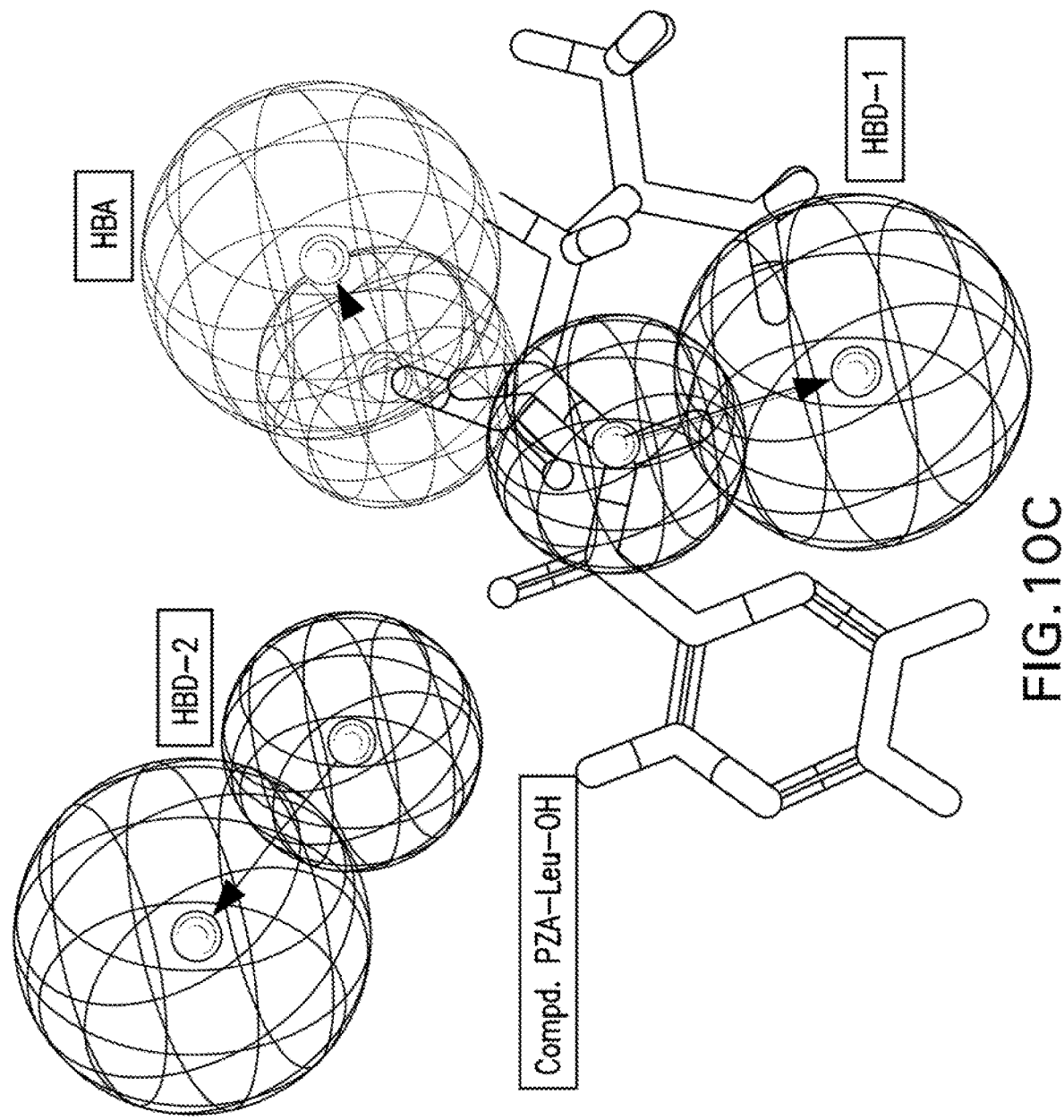
Figure 10D:
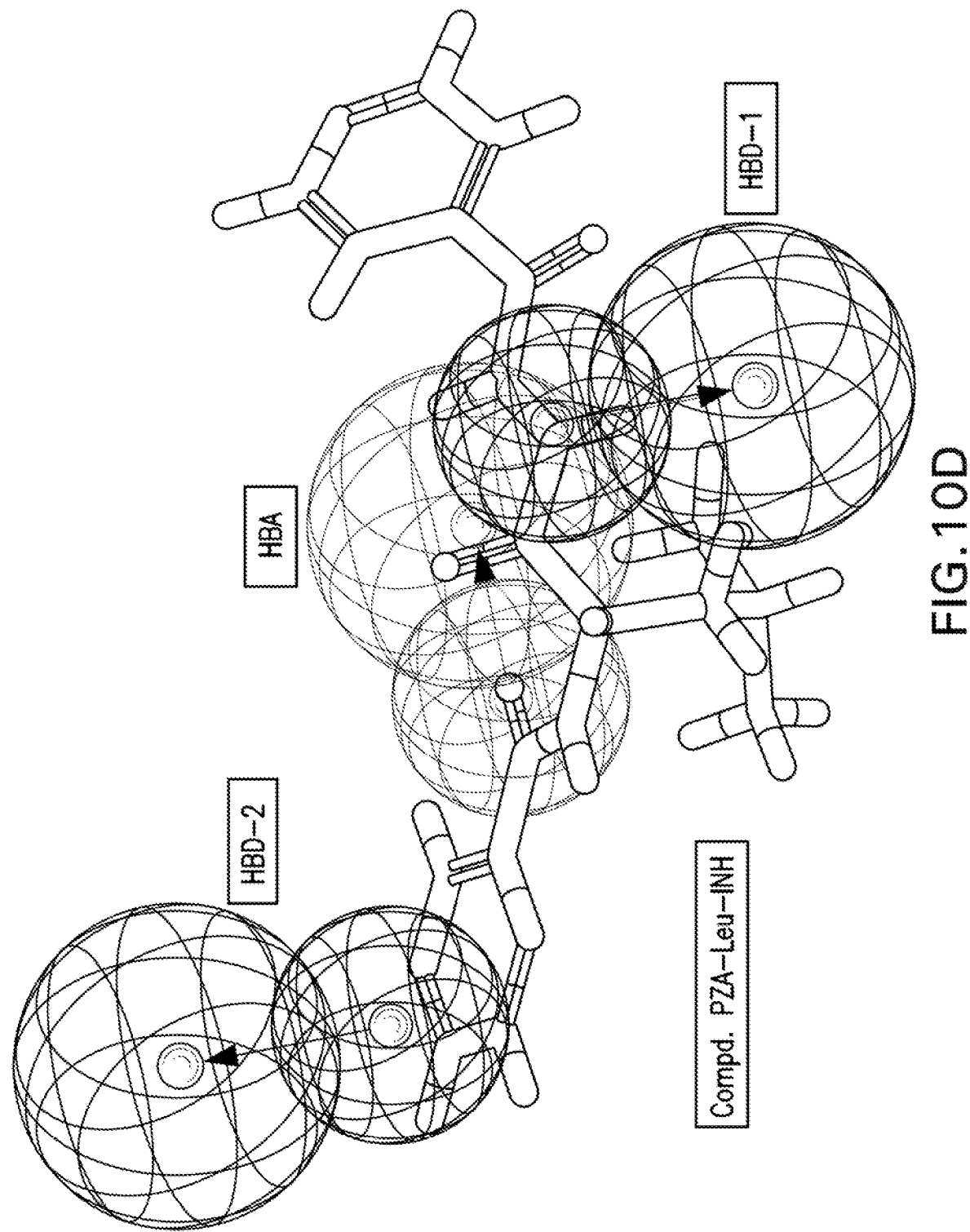
Figure 10E:
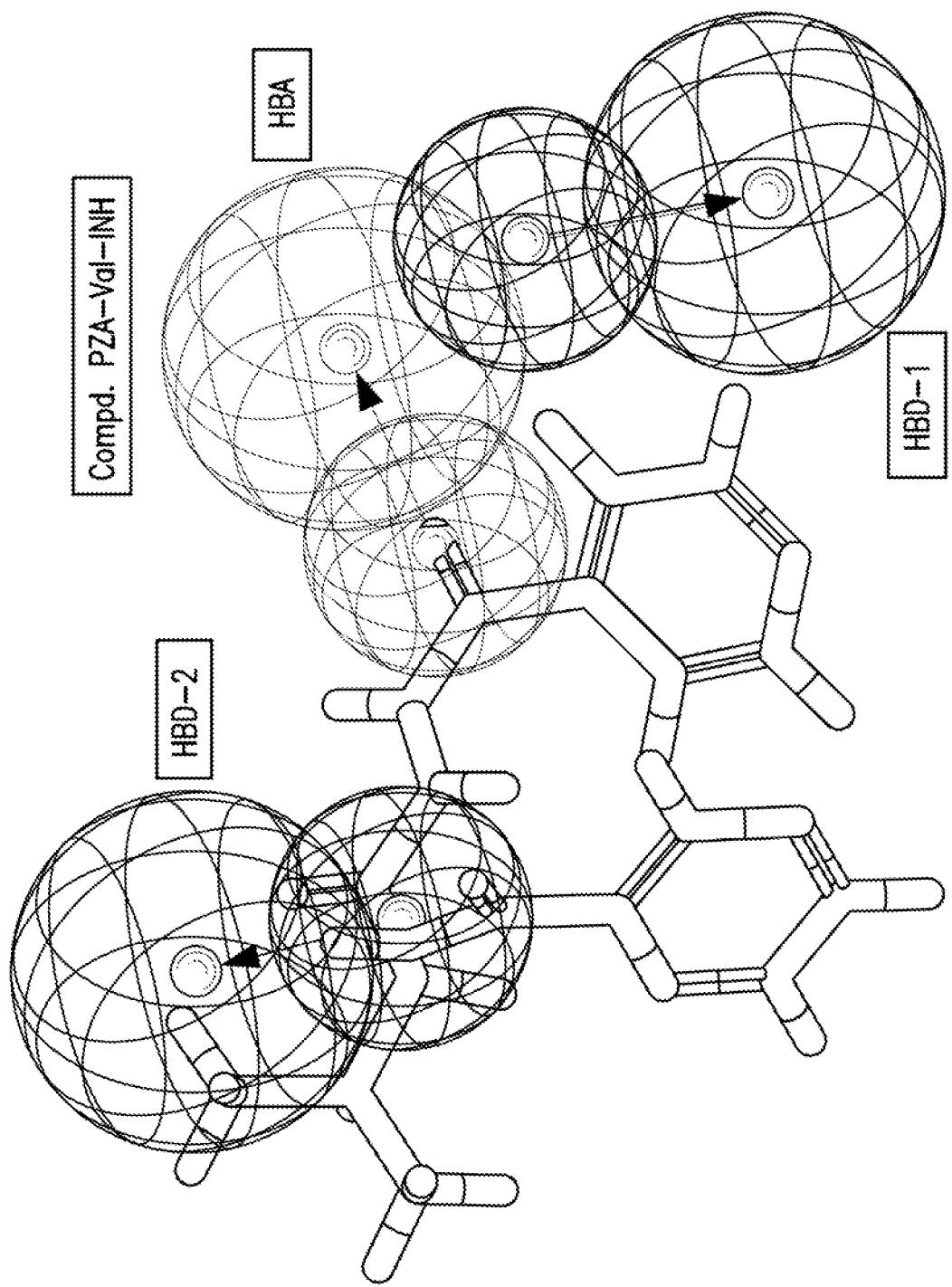
Figure 10F:
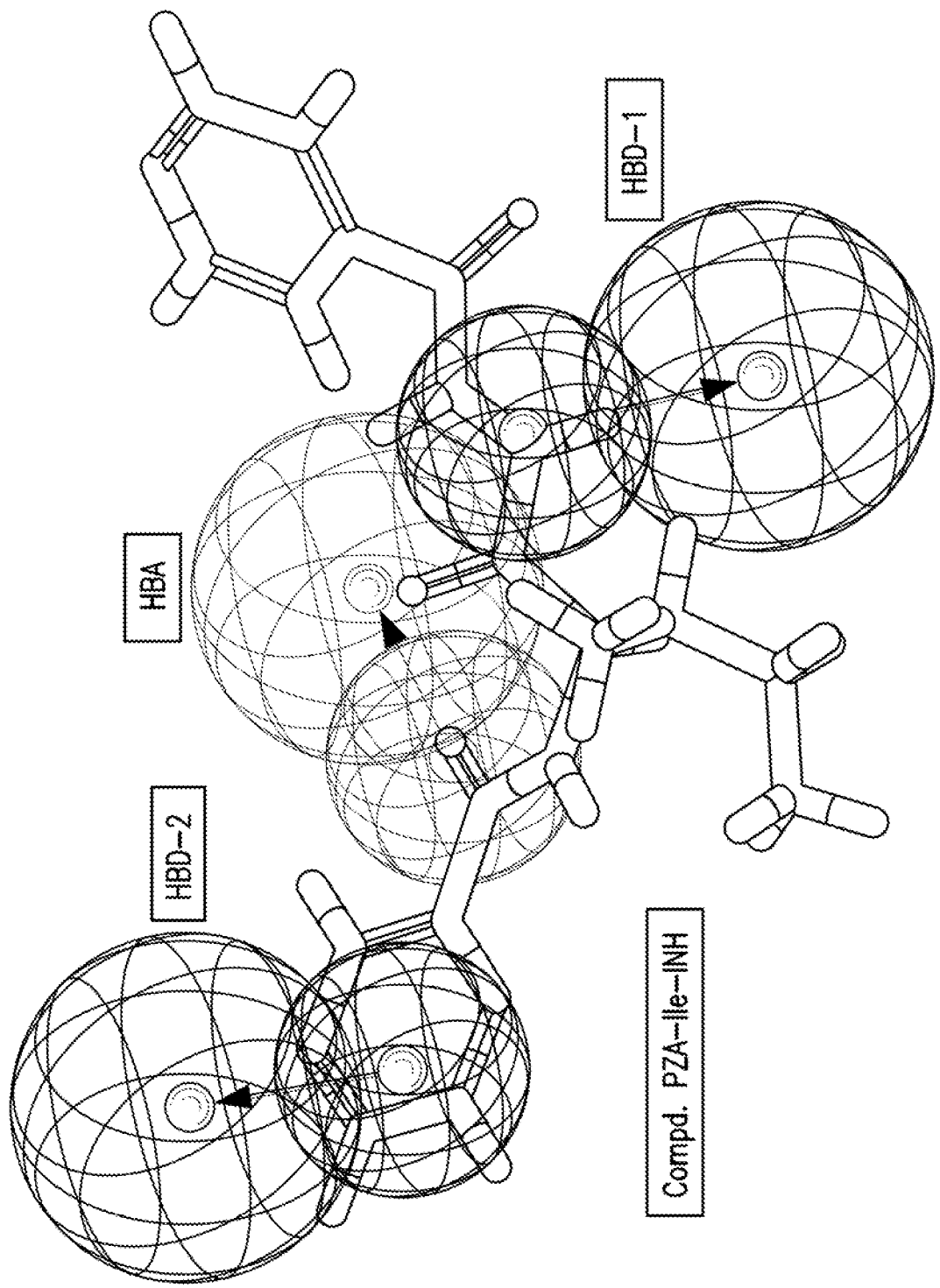
Figure 10G:
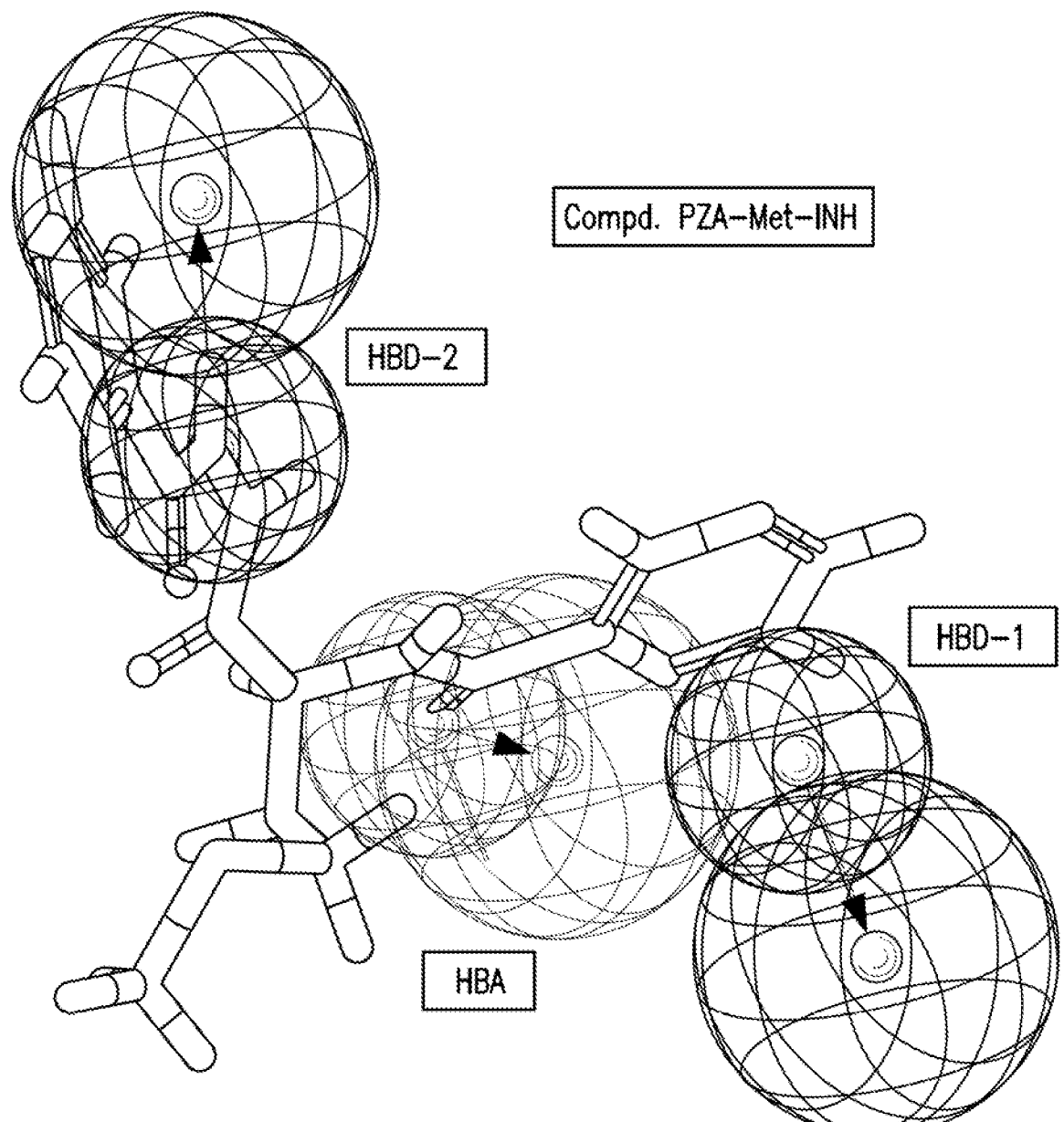
Figure 10H:
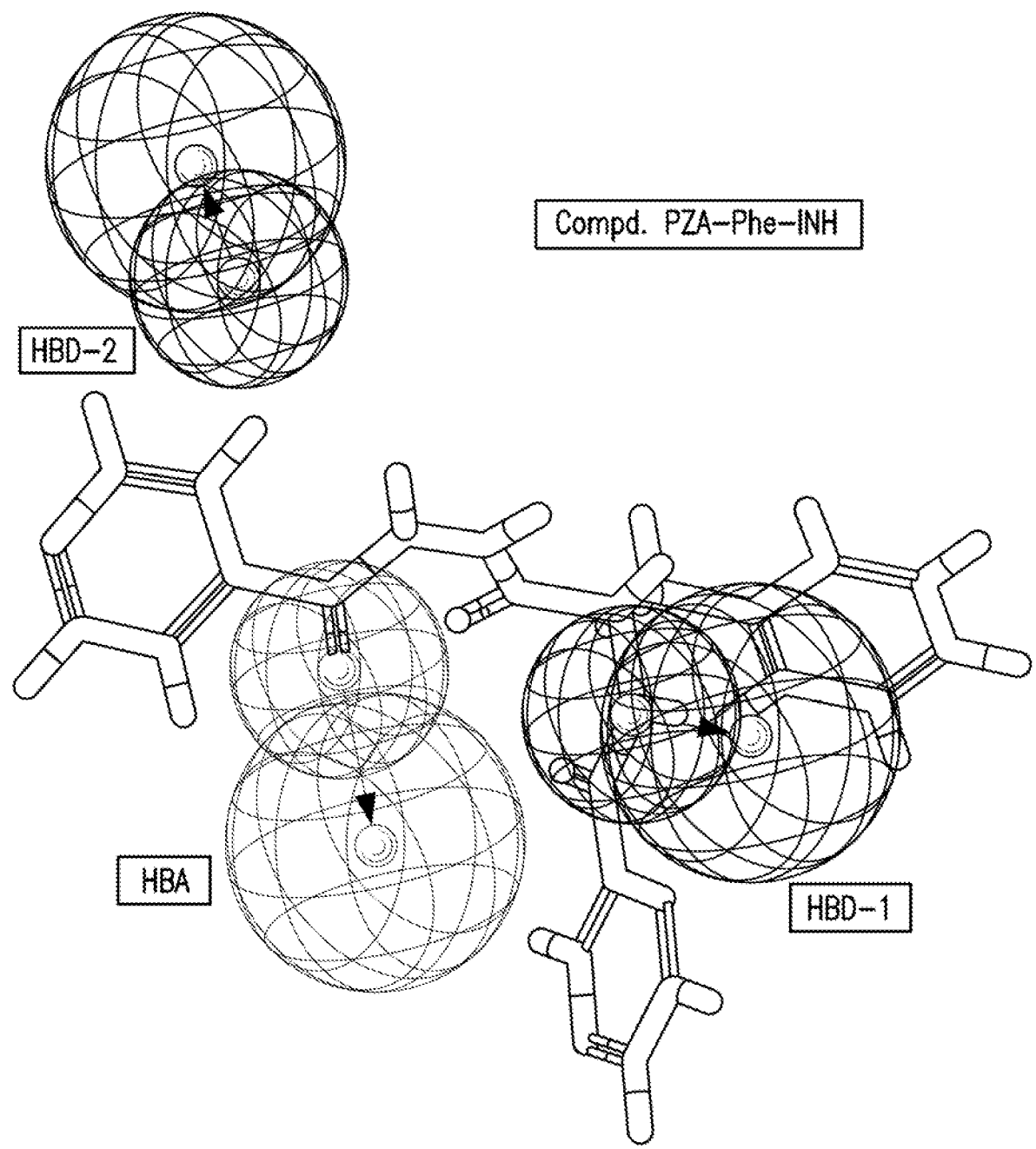
Figure 10I:
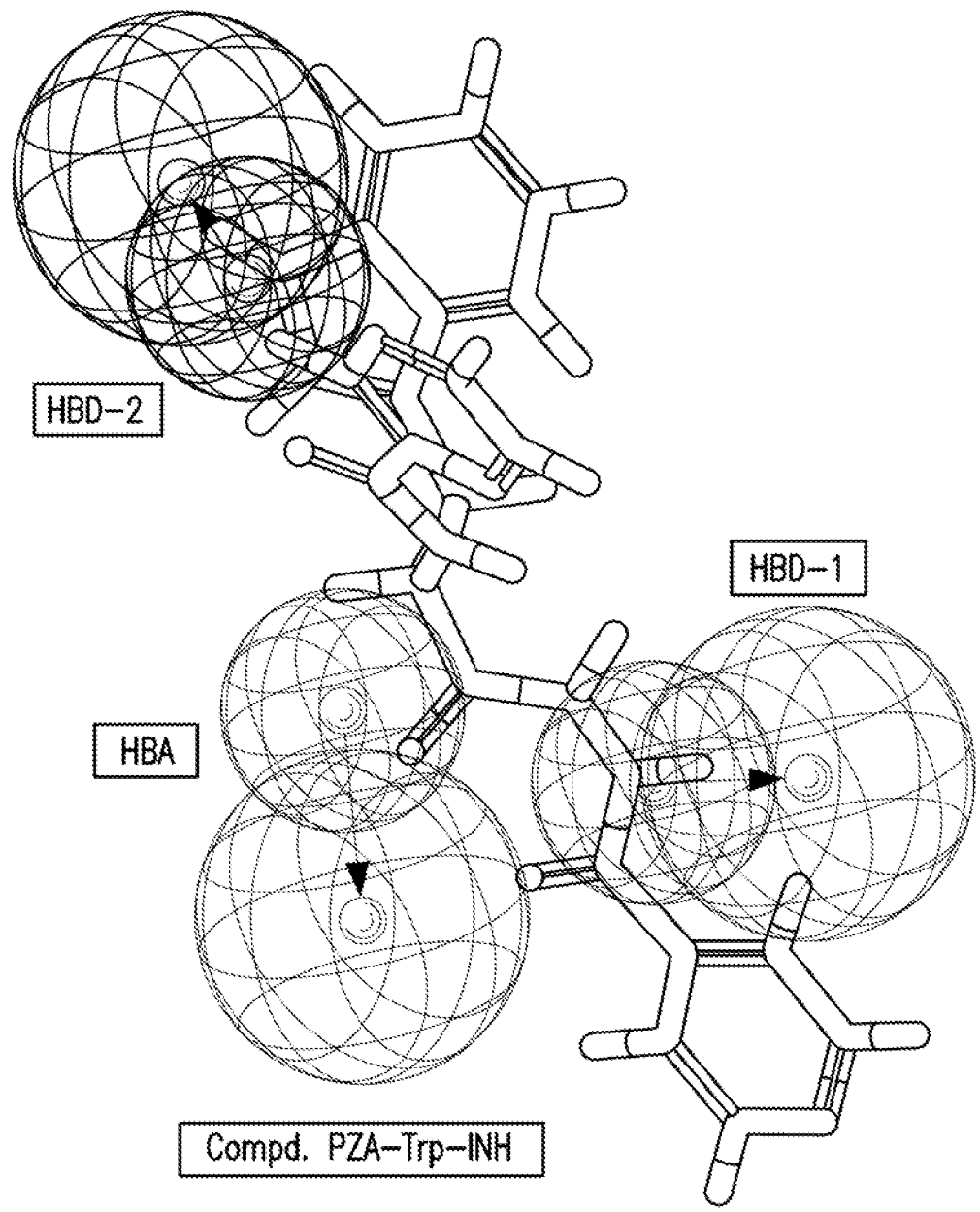
Figure 10K:
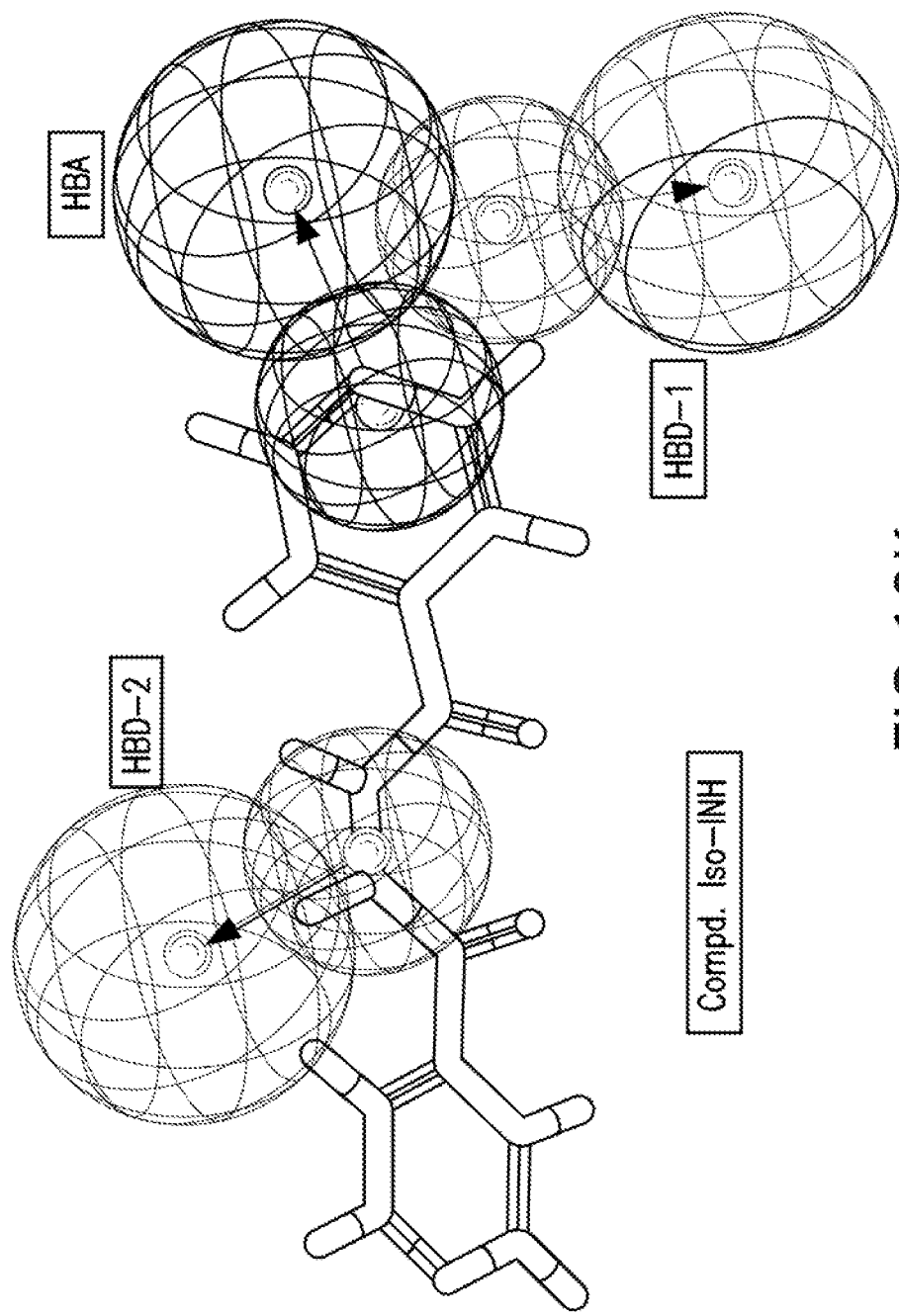
Figure 11:
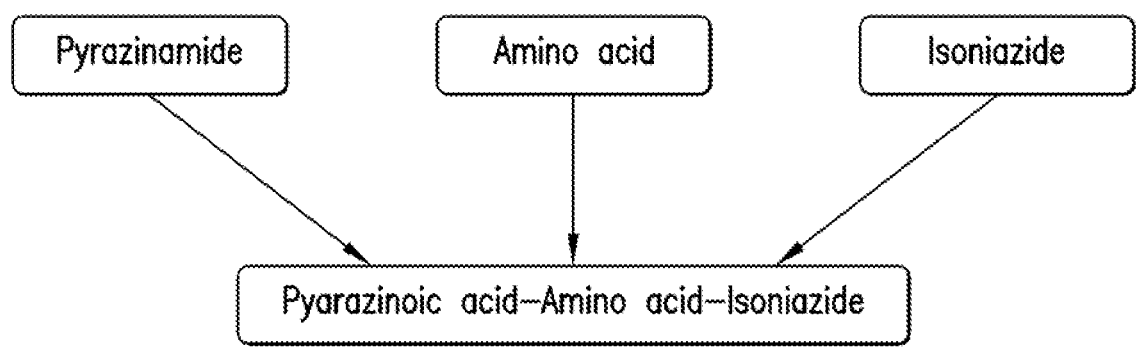
FIG. 11 is a schematic showing a general approach to producing PZA conjugates.

Three chemical features [two hydrogen bonding donors (HBD-1, HBD-2) and one hydrogen bonding acceptor (HBA)] were exhibited by the 3D-pharmacophore due to the tested bioactive agents against *Mycobacterium fortuitum* (FIGS. 9A-9B). PZA-Trp-INH, which is one of the highest potent hits synthesized against M. fortuitum reveals alignment of isonicotinic acid hydrazide N-1 with HBD-1 ($MIC_{observed}$=46.6, $MIC_{estimated}$=44.7 mM). However, N-1 and N-2 of the hydrazide moiety of compounds PZA-Met-INH and PZA-Leu-INH are aligned with HBD-2 and HBD-1, respectively ($MIC_{observed}$=53.4, 56.1, $MIC_{estimated}$=50.6, 52.7 mM for PZA-Met-INH and PZA-Leu-INH, respectively). Meanwhile, the nitrogen atom of pyrazinecarboxamide function of compounds PZA-Phe-INH and PZA-Val-INH are aligned with HBD-1 and HBD-2, respectively ($MIC_{observed}$=51.2, 58.4, $MIC_{estimated}$=48.0, 56.9 mM for PZA-Phe-INH and PZA-Val-INH, respectively) (Table 11, FIGS. 10A-10K).

From all the above 3D-pharmacophoric model observations, the alignment of various nitrogen atoms with hydrogen bonding donor functions is the main controlling parameter revealing bio-properties. This seems a common observation between the two techniques utilized in the present computational study (2D-QSAR and 3D-pharmacophore) where the 2D-QSAR studies reveal important descriptors dealing with nitrogen atoms governing bio-properties (max. e-n attraction for bond C—N for the QSAR model of M. marinum and max. e-e repulsion for atom N, avg. electroph. react. index for atom N for the QSAR model of M. fortuitum).

TABLE 11

Estimated/predicted activity values for the tested compounds mapped with the generated 3D-pharmacore models.

| Entry | Compound | Mycobacterium marinum | | Mycobacterium fortuitum | |
|---|---|---|---|---|---|
| | | Observed MIC, mM | Estimated MIC, mM | Observed MIC, mM | Estimated MIC, mM |
| 1 | PZA | 81.2 | 138.5 | 81.2 | 88.2 |
| 2 | INH | 72.9 | 77.4 | 145.8 | 96.7 |
| 3 | PZA-Leu-OH | 84.3 | 83.2 | 84.3 | 91.5 |
| 4 | PZA-Leu-INH | 56.1 | 46.9 | 56.1 | 52.7 |
| 5 | PZA-Val-INH | 58.4 | 43.7 | 58.4 | 56.9 |
| 6 | PZA-Ile-INH | 56.1 | 45.2 | 56.1 | 52.3 |
| 7 | PZA-Met-INH | 26.7 | 33.4 | 53.4 | 50.6 |
| 8 | PZA-Phe-INH | 51.2 | 39.3 | 51.2 | 48.0 |
| 9 | PZA-Trp-INH | 46.6 | 38.1 | 46.6 | 44.7 |
| 10 | PZA-INH | 41.1 | 67.4 | 41.1 | 75.7 |
| 11 | Iso-INH | 82.6 | 65.2 | 82.6 | 75.8 |

Example 7: Synthesis of POA-2° Amines and POA-INH Hybrid Conjugates

Figure 12A:
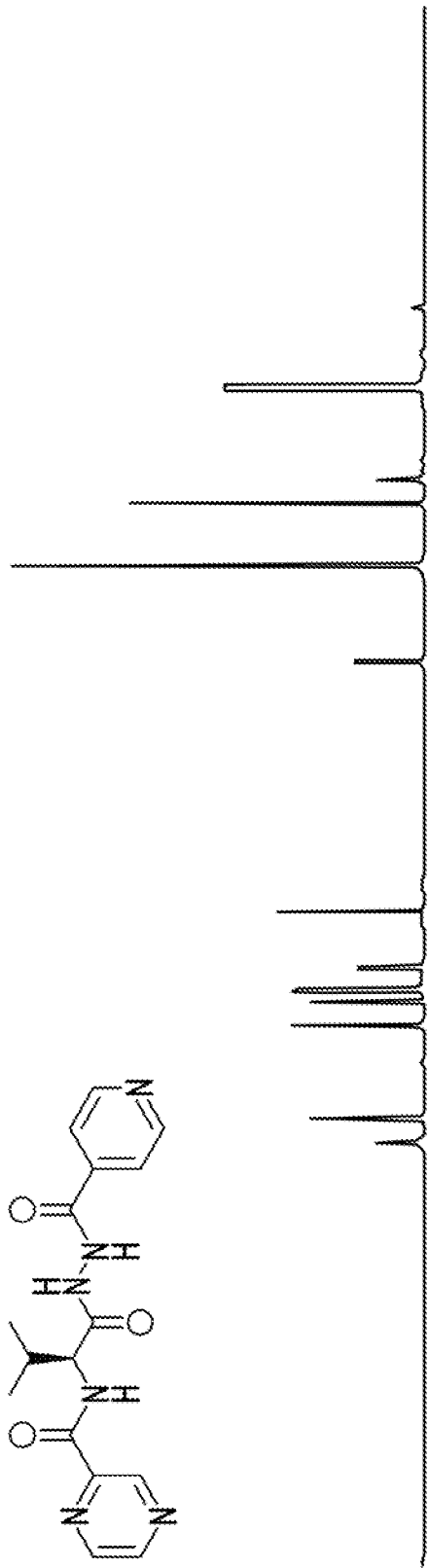
FIG. 12A is the 1H NMR of POA-L-Val-INH.
Figure 12B:
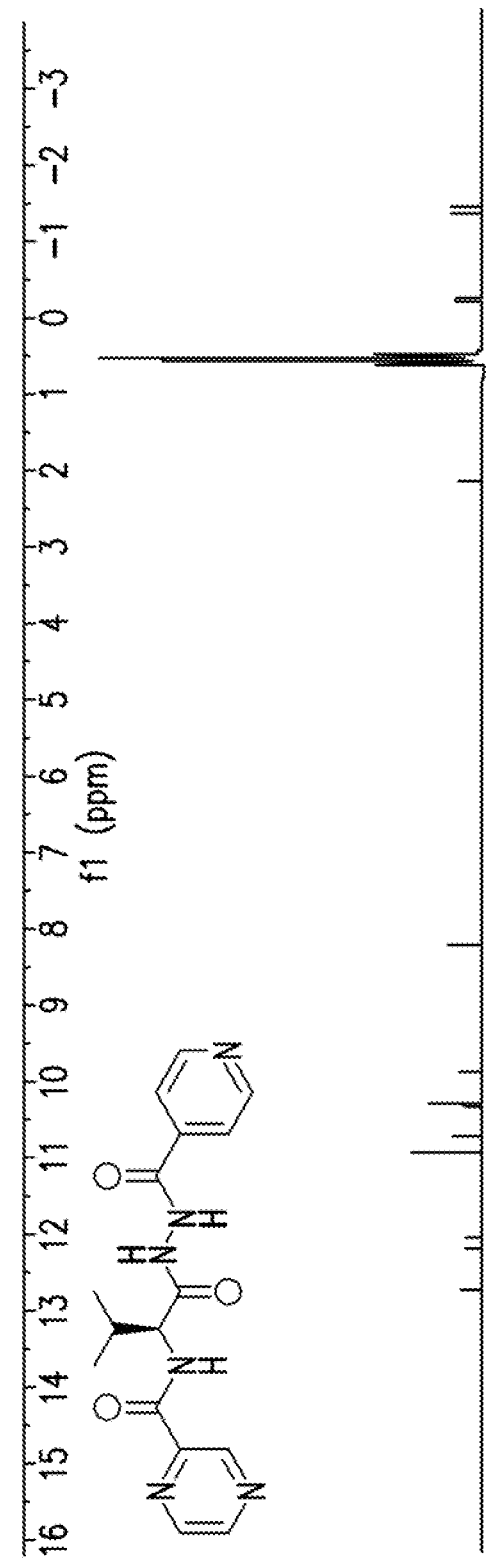
FIG. 12B is the 13C NMR of POA-L-Val-INH.

Results:

An efficient methodology for synthesizing various POA-2° amines and POA-INH hybrid conjugates in high yields and purity was developed by utilizing the benzotriazolides of POA-amino acids. All the synthesized conjugates were fully characterized by spectroscopy methods (FIG. 12A-12B). The retention of the chirality was studied by optical rotation and chiral HPLC of L and DL amino acid derivatives. POA-AA-Het and POA-AA-INH hybrid conjugates were successfully synthesized in good yields.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A pyrazinamide conjugate having the general structure

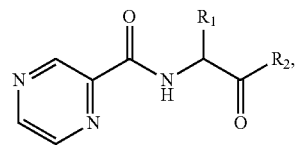

(1)

wherein:

$R_1$ is $CH_2CH(CH_3)_2$, $CH(CH_2CH_3)CH_3$, or $CH_2$-indolyl; and $R_2$ is nicotinic acid, isoniazid, or ethionamide.

2. A pyrazinamide conjugate having the general structure

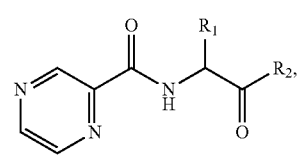

(1)

wherein:

$R_1$ is $CH_2CH(CH_3)_2$, $CH(CH_2CH_3)CH_3$, or $CH_2$-indolyl; and $R_2$ is isoniazid.

3. A pyrazinamide conjugate having the general structure

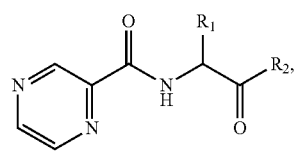

(1)

wherein:

$R_1$ is $CH_2CH(CH_3)_2$, $CH(CH_3)_2$, $CH(CH_2CH_3)CH_3$, $CH_2CH_2SCH_3$, $CH_2Ph$, or $CH_2$-indolyl; and $R_2$ is isoniazid.

4. The pyrazinamide conjugate of claim 2, wherein the structure of the conjugate is:

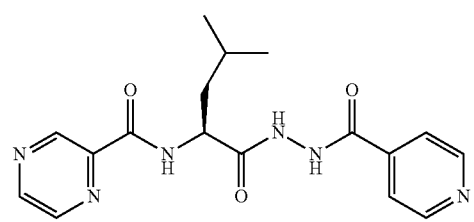

(9)

PZA-Leu-INH

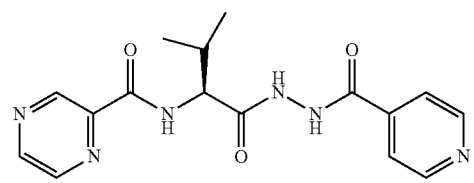

(10)

PZA-Val-INH

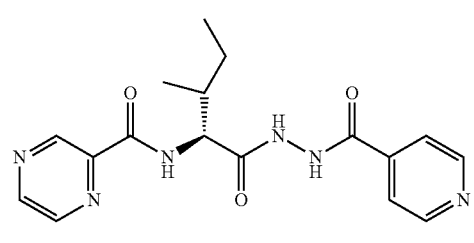

(11)

PZA-Ile-INH

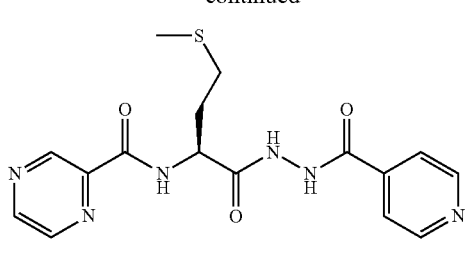

PZA-Met-INH

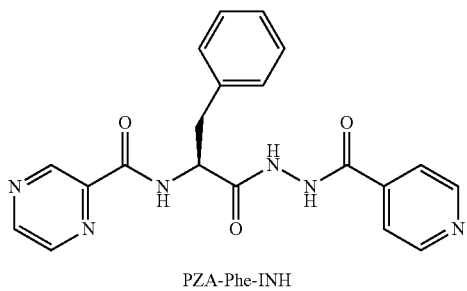 [SMILES: O=C(NNC(=O)[C@H](Cc1ccccc1)NC(=O)c1cnccn1)c1ccncc1]

PZA-Phe-INH

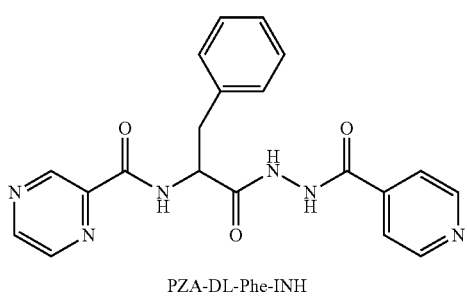

PZA-DL-Phe-INH

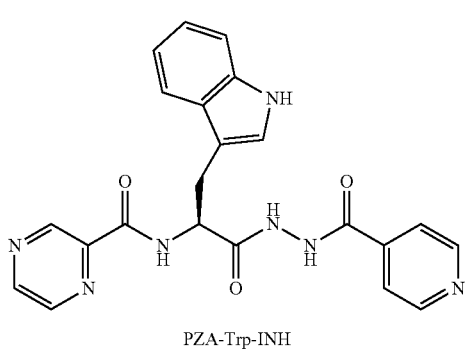 [SMILES: O=C(NNC(=O)[C@H](Cc1c[nH]c2ccccc12)NC(=O)c1cnccn1)c1ccncc1]

PZA-Trp-INH

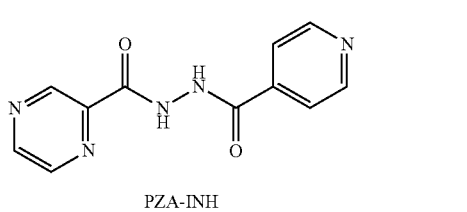 [SMILES: O=C(NNC(=O)c1cnccn1)c1ccncc1]

PZA-INH

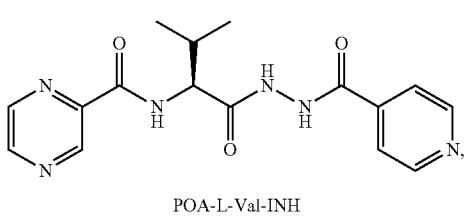

POA-L-Val-INH

5. A pyrazinamide conjugate having the structure

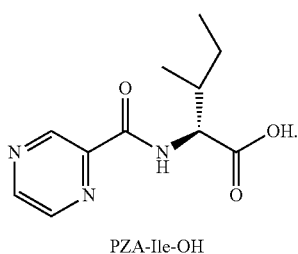

PZA-Ile-OH

6. A pharmaceutical composition comprising a therapeutically effective amount the compound of claim 2.

7. The pharmaceutical composition of claim 6, wherein the composition is formulated for oral administration.

8. The pharmaceutical composition of claim 6, wherein the composition is formulated for parenteral administered composition.

9. The pharmaceutical composition of claim 6, further comprising a pharmaceutically acceptable excipient.

10. A method for treating a subject with a bacterial infection, comprising administering to the subject a therapeutically effective amount of the pyrazinamide conjugate of claim 2.

11. The method of claim 10, wherein the bacterial infection is tuberculosis.

12. The method of claim 10, wherein the bacterial infection is caused by one or more bacteria selected from the group consisting of *Mycobacterium marinum, Mycobacterium fortuitum, Mycobacterium tuberculosis, Staphylococcus aureus, Enterococcus faecalis, Klebsiella pneumonia, Proteus vulgaris, Pseudomonas aeruginosa,* and *Proteus vulgaris.*

13. A method for treating a subject with a bacterial infection, comprising administering to the subject a therapeutically effective amount of the pyrazinamide conjugate of claim 4.

14. The method of claim 13, wherein the bacterial infection is tuberculosis.

15. The method of claim 13, wherein the bacterial infection is caused by one or more bacteria selected from the group consisting of *Mycobacterium marinum, Mycobacterium fortuitum, Mycobacterium tuberculosis, Staphylococcus aureus, Enterococcus faecalis, Klebsiella pneumonia, Proteus vulgaris, Pseudomonas aeruginosa,* and *Proteus vulgaris.*

16. The method of claim 13, wherein the pyrazinamide conjugate is administered to the subject according to a regimen selected from 7 days per week for 8 weeks, 5 days per week for 8 weeks, 3 times per week for 7 weeks, or 7 days per week for 2 weeks then twice weekly for 6 weeks.

17. The method of claim 13, wherein a second therapeutic is jointly administered to the subject serially or in combination or alternation with the pyrazinamide conjugate.

* * * * *